United States Patent [19]

Buchecker et al.

[11] Patent Number: 5,013,477
[45] Date of Patent: May 7, 1991

[54] ALKENYLBICYCLOHEXANE LIQUID CRYSTALS

[75] Inventors: Richard Buchecker, Zurich; Martin Schadt, Seltisberg, both of Switzerland

[73] Assignee: Hoffmann-La Roche Inc., Nutley, N.J.

[21] Appl. No.: 262,653

[22] Filed: Oct. 26, 1988

[30] Foreign Application Priority Data

Nov. 6, 1987 [CH] Switzerland ............... 4354/87
Aug. 24, 1988 [CH] Switzerland ............... 3137/88

[51] Int. Cl.$^5$ .................. C09K 19/30; C07C 41/00
[52] U.S. Cl. ................ 252/299.63; 252/299.01; 350/350 R; 350/350 S; 568/664
[58] Field of Search ........... 252/299.63, 299.01, 252/299.5; 350/350 R, 350 S; 568/664

[56] References Cited

U.S. PATENT DOCUMENTS

| SN 53,778 | 6/1886 | Petrazilka et al. | 252/299.63 |
| 4,565,425 | 1/1986 | Petrzilka et al. | 252/299.63 |
| 4,621,901 | 11/1986 | Petrzilka et al. | 252/299.63 |
| 4,622,164 | 11/1986 | Eidenschink et al. | 252/299.63 |
| 4,654,421 | 3/1987 | Tanaka et al. | 252/299.63 |
| 4,676,604 | 6/1987 | Petrzilka | 252/299.63 |
| 4,709,030 | 11/1987 | Petrzilka | 252/299.63 |

FOREIGN PATENT DOCUMENTS

| 268198 | 5/1988 | European Pat. Off. | 252/299.63 |
| 3321373 | 12/1984 | Fed. Rep. of Germany | 252/299.63 |
| 3601452 | 7/1987 | Fed. Rep. of Germany | 252/299.63 |
| 59-70624 | 4/1984 | Japan | 252/299.63 |
| 60-69040 | 4/1985 | Japan | 252/299.63 |
| 61-27928 | 2/1986 | Japan | 252/299.63 |
| 61-257935 | 11/1986 | Japan | 252/299.63 |
| 63-3086 | 1/1988 | Japan | 252/299.63 |

OTHER PUBLICATIONS

Petrzilka, M. et al., Mol. DL. Cryst. Liq. Cryst., vol. 148, pp. 123-143 (1987).
Petrazilka et al., Ser. No. 53,778, filed Jun. 6, 1986.

Primary Examiner—John S. Maples
Assistant Examiner—Richard Treanor
Attorney, Agent, or Firm—George M. Gould; George W. Johnston; Bernard S. Leon

[57] ABSTRACT

Compounds of the formula

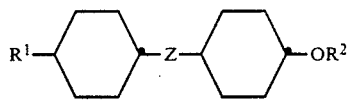

I wherein Z represents a single covalent bond or —CH$_2$CH$_2$—, R$^1$ denotes 1E-alkenyl with 2–10 carbon atoms or 3E-alkenyl with 4–10 carbon atoms and R$^2$ is alkyl with 1–10 carbon atoms, 2E-alkenyl with 3–10 carbon atoms or 3-alkenyl with 4–10 carbon atoms, as well as their use in liquid crystalline mixtures and for electro-optical purposes.

15 Claims, No Drawings

ALKENYLBICYCLOHEXANE LIQUID CRYSTALS

BACKGROUND

1. Field of the Invention

The present invention is concerned with novel alkenylbicyclohexanes, liquid crystalline mixtures which contain these compounds as well as their use for electro-optical purposes.

2. Description

Liquid crystals are used primarily as dielectrics in indicating devices, since the optical properties of such substances can be influenced by an applied voltage. Electro-optical devices based on liquid crystals are well-known to the person skilled in the art and can be based on various effects. Such devices are, for example, cells having dynamic scattering, DAP cells (deformation of aligned phases), guest/host cells, TN cells having a twisted nematic structure, STN cells ("super-twisted nematic"), SBE cells ("super-birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields and electromagnetic radiation. Further, the liquid crystal materials should have a low viscosity and short response times, low threshold potentials and a high contrast in the cells. Furthermore, at the usual operating temperatures, that is, in a range below and above room temperature which is as wide as possible, they should have a suitable mesophase, for example a nematic or cholesteric mesophase for the aforementioned cells. Since liquid crystals are generally used as mixtures of several components, it is important that the components have a good miscibility with one another. Further properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible.

There has recently been an increased interest in materials having a low optical anisotropy, especially for actively addressed liquid crystal indicators such as MIM applications (metal-isolator-metal) or TFT applications ("thin film transistor") in television sets. The known liquid crystalline compounds having a low optical anisotropy possess, however, for the most part highly ordered smectic phases or lead to an undesired increase in the threshold potential, the viscosity and/or the response times.

SUMMARY OF THE INVENTION

The present invention provides compounds of the formula

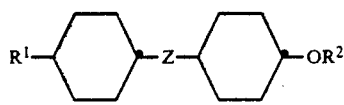

wherein Z represents a single covalent bond or —$CH_2CH_2$—, $R^1$ denotes 1E-alkenyl with 2–10 carbon atoms or 3E-alkenyl with 4–10 carbon atoms and $R^2$ is alkyl with 1–10 carbon atoms, 2E-alkenyl with 3–10 carbon atoms or 3-alkenyl with 4–10 carbon atoms.

The compounds in accordance with the invention are liquid crystals having a very low optical anisotropy and comparatively high clearing points. In contrast to previously known bicyclohexanes they have a relatively broad nematic mesophase or in the case of the optically active compounds a cholesteric mesophase. Highly ordered smectic phases are suppressed. Further, the compounds in accordance with the invention have comparatively low viscosities and permit rapid switching times. They have a good solubility in other liquid crystal materials and are especially suitable as components of nematic and cholesteric mixtures.

DETAILED DESCRIPTION OF THE INVENTION

The present invention is directed to alkenybicyclohexane compounds of the formula

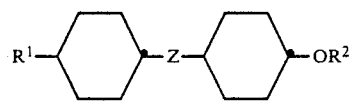

wherein Z is a single covalent bond or —$CH_2CH_2$—, $R^1$ is 1E-alkenyl with 2–10 carbon atoms or 3E-alkenyl with 4–10 carbon atoms and $R^2$ is alkyl with 1–10 carbon atoms, 2E-alkenyl with 3–10 carbon atoms or 3-alkenyl with 4–10 carbon atoms. Formula I embraces the compounds of the formulas

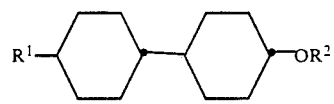

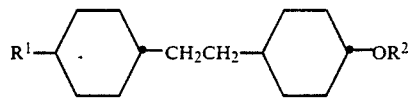

wherein $R^1$ and $R^2$ have the above significances.

$R^1$ embraces the straight-chain residues vinyl, 1E-propenyl, 1E-butenyl, 1E-pentenyl, 1E-hexenyl, 1E-heptenyl, 1E-octenyl, 1E-nonenyl, 1E-decenyl, 3-butenyl, 3E-pentenyl, 3E-hexenyl, 3E-heptenyl, 3E-octenyl, 3E-nonenyl and 3E-decenyl as well as branched-chain, optionally optically active residues such as 5-methyl-3E-heptenyl and the like. The straight-chain residues are generally preferred. Further, 1E-alkenyl residues with 2–7 carbon atoms and 3E-alkenyl residues with 4–7 carbon atoms are generally preferred.

The term "alkyl" (e.g., for $R^2$) embraces the straight-chain residues methyl, ethyl, propyl, butyl, pentyl, hexyl, heptyl, octyl, nonyl and decyl as well as branched-chain, optionally optically active residues such as sec-butyl, 2-methylbutyl, 3-methylpentyl, 4-methylhexyl and the like. The term "lower alkyl" means alkyl of 1 to 4 carbon atoms.

The term "2E-alkenyl" (e.g., for $R^2$) embraces the straight-chain residues allyl, 2E-butenyl, 2E-pentenyl, 2E-hexenyl, 2E-heptenyl, 2E-octenyl, 2E-nonenyl and 2E-decenyl as well as branched-chain, optionally optically active residues such as 4-methyl-2E-hexenyl and the like.

The term "3-alkenyl" (e.g., for $R^2$) embraces the straight-chain residues 3-butenyl, 3-pentenyl, 3-hexenyl, 3-heptenyl, 3-octenyl, 3-nonenyl and 3-decenyl as well as branched-chain residues such as 5-methyl-3-heptenyl and the like. In the case of residues which can be present in E- or Z-form, the Z-form is generally preferred, that is, preferred residues are 3-butenyl, 3Z-pentenyl, 3Z-hexenyl etc.

The residue $R^2$ preferably has up to 6 carbon atoms. In formulas I, Ia and Ib above $R^2$ therefore preferably is alkyl with 1–6 carbon atoms, 2E-alkenyl with 3–6 carbon atoms or 3-alkenyl with 4–6 carbon atoms.

The term "halo" denotes fluoro, chloro, bromo and iodo.

Of the compounds of formulas I, Ia and Ib there are generally preferred those in which $R^1$ and $R^2$ are straight-chain residues.

Those compounds of formulas I, Ia and Ib in which $R^1$ denotes a 3E-alkenyl residue are generally preferred. However, the compounds of formulas I, Ia and Ib in which $R^1$ denotes a 1E-alkenyl residue are preferred, inter alia, when short side-chains are desired.

The optically active compounds of formulas I, Ia and Ib are suitable as chiral doping agents. In general, there are preferred those in which $R^1$ is a straight-chain residue and $R^2$ is a branched-chain, optically active residue.

The compounds of formula I can be prepared in a manner known per se, for example by etherifying the corresponding cyclohexanol derivative with a compound of the formula $R^2X$, wherein $R^2$ has the above significance and X denotes chlorine, bromine or iodine, or by forming the group $R^1$ in a Wittig reaction with an alkyl-triphenylphosphonium chloride or bromide starting from the corresponding cyclohexanecarboxaldehyde or 3-cyclohexylpropionaldehyde. The preparation can be effected under the conditions which are usual for these methods and is illustrated in more detail in the Synthesis Examples.

The compounds of formula I can be used in the form or, mixtures with one another and/or with other liquid crystal components such as for example, with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexylbiphenyls, cyclohexylphenylpyrimidines and the like. Such substances are known to the person skilled in the art and many of them are, moreover, commercially obtainable.

The liquid crystalline mixtures in accordance with the invention contain at least two components, of which at least one component is a compound of formula I. A second component and optionally further components can be further compounds of formula I and/or other liquid crystal components.

The compounds of formula I are especially suitable for nematic mixtures or, insofar as at least one component of the mixture is optically active, also for cholesteric mixtures. A preferred field of application is their use as dielectrics in liquid crystal indicating devices having a twisted nematic liquid crystal structure such as TN cells, STN cells, SBE cells and OMI cells. Preferred mixtures are therefore those which contain one or more compounds of formula I and one or more compounds having positive dielectric anisotropy.

Their use as dielectrics in liquid crystal indicating devices having a highly twisted nematic liquid crystal layer is especially preferred, whereby as highly twisted liquid crystal layers there are to be understood those which are twisted by more than 90°. For this field of application the liquid crystalline mixture conveniently contains one or more compounds of formula I and one or more compounds having positive dielectric anisotropy, with at least one component of the mixture being optically active. The optically active component or components can be compounds of formula I, compounds having positive dielectric anisotropy and/or other usual doping agents such as optically active biphenyls, esters and the like. The optically active material is conveniently used in an amount such that the ratio between the layer thickness (in the cell) and the natural pitch of the total mixture amounts to about 0.2 to 1.3, that is, so that in the case of today's usual layer thicknesses of about 5–10 mm the natural pitch amounts to about 4–50 mm.

Having regard to the good solubility of the compounds of formula I in other liquid crystal materials and having regard to their good miscibility with one another, the amount of compounds of formula I in the mixtures in accordance with the invention can be relatively high and can amount to, for example, about 1–70 wt. %. An amount of about 3–40 wt. %, especially about 5–30 wt. %, of compounds of formula I is generally preferred.

The mixtures in accordance with the invention preferably contain, besides one or more compounds of formula I, one or more compounds from the group of compounds of the formulas

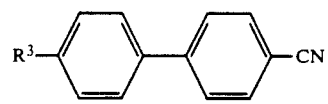

II

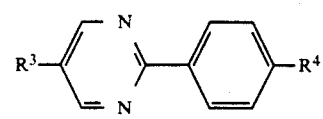

III

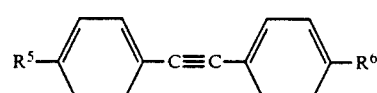

IV

-continued
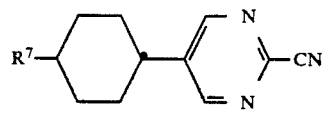 V
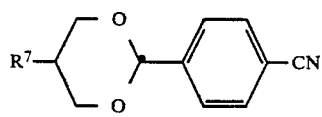 VI
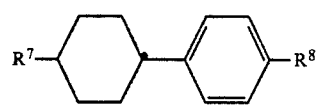 VII
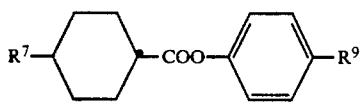 VIII
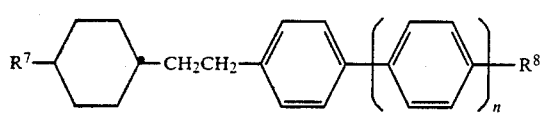 IX
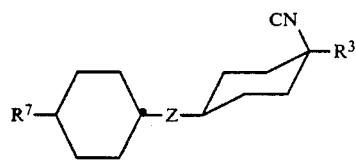 X
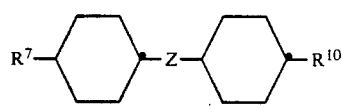 XI
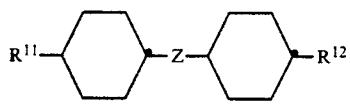 XII
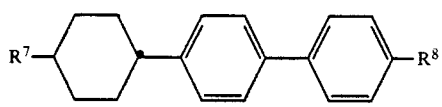 XIII
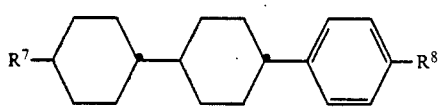 XIV
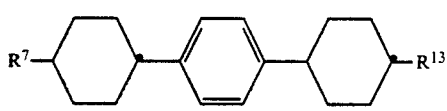 XV
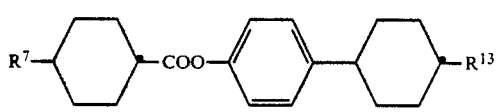 XVI
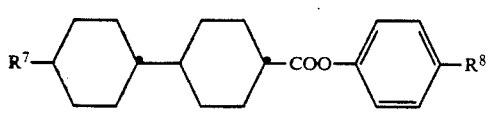 XVII

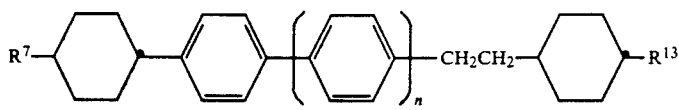

XVIII

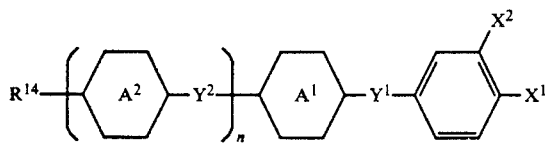

XIX wherein $R^3$ is alkyl, 3E-alkenyl or 4-alkenyl; $R^4$ represents cyano or fluoro; $R^5$ and $R^6$ denote alkyl or alkoxy; $R^7$ and $R^{13}$ each independently are alkyl, 1E-alkenyl, 3E-alkenyl or 4-alkenyl; $R^8$ denotes cyano, alkyl, 1E-alkenyl, 3E-alkenyl, 4-alkenyl, alkoxy, 2E-alkenyloxy or 3-alkenyloxy; $R^9$ is alkoxy, 2E-alkenyloxy or 3-alkenyloxy; n stands for the number 0 or 1; Z represents a single covalent bond or —CH$_2$CH$_2$—; $R^{10}$ is cyano, alkyl, 1E-alkenyl, 3E-alkenyl or 4-alkenyl; $R^{11}$ denotes alkyl or 4-alkenyl; $R^{12}$ represents alkoxy, 2E-alkenyloxy or 3-alkenyloxy; $X^1$ denotes fluorine or chlorine and $X^2$ denotes hydrogen, fluorine or chlorine; $R^{14}$ is alkyl, 3E-alkenyl, 4-alkenyl, alkoxy, 2E-alkenyloxy or 3-alkenyloxy; one of the groups $Y^1$ and $Y^2$ is a single covalent bond, —COO—, —OOC—, —CH$_2$CH$_2$—, —CH$_2$O— or —OCH$_2$— and the other of the groups $Y^1$ and $Y^2$ is a single covalent bond; and rings $A^1$ and $A^2$ each independently represent substituted or unsubstituted trans-1,4-cyclohexylene, in which optionally 2 non-adjacent CH$_2$ groups are replaced by oxygen, or substituted or unsubstituted 1,4-phenylene, in which optionally 1 CH group or 2 CH groups is/are replaced by nitrogen.

The term "substituted or unsubstituted trans-1,4-cyclohexylene, in which optionally 2 non-adjacent CH$_2$ groups are replaced by oxygen" embraces especially trans-1,4-cyclohexylene and trans-m-dioxane-2,5-diyl as well as rings which are substituted with substituents which are usual in liquid crystals such as cyano, methyl, fluorine or chlorine, for example 1-cyano-trans-1,4-cyclohexylene or 2-methyl-trans-1,4-cyclohexylene.

The term "substituted or unsubstituted 1,4-phenylene, in which optionally 1 CH group or 2 CH groups is/are replaced by nitrogen" embraces especially 1,4-phenylene, pyridine-2,5-diyl, pyrazine-2,5-diyl and pyrimidine-2,5-diyl as well as rings which are substituted with substituents which are usual in liquid crystals such as cyano, lower alkyl (e.g. methyl), halo (e.g. fluorine or chlorine) for example 2-cyano-1,4-phenylene, 2-fluoro-1,4-phenylene, 2-chloro-1,4-phenylene or 2-methyl-1,4-phenylene.

The cyano and halo compounds of formulas II, III, V, VI, VII, IX, XI, XIII, XIV, XVII and XIX are preferred mixture components having positive dielectric anisotropy. Preferably, the total mixture contains about 20-70 wt. %, especially about 25-50 wt. %, of one or more of these compounds.

The compounds of formulas V-XIX, especially the compounds of formula X, XI, XII, XIV, XV, XVI, XVII and XVIII as well as the compounds of formula XIX in which rings $A^1$ and $A^2$ are trans-1,4-cyclohexylene, are preferred mixture components for the production of a low optical anisotropy in the total mixture.

Those mixtures which contain, in addition to one or more compounds of formula I, one or more compounds of formula V, VII, XI, XII, XIV, XV and/or XIX are generally especially preferred.

The compounds of formula XI in which $R^{10}$ is cyano and the compounds of formula XII in which $R^{11}$ is 4-alkenyl are novel. Also novel are those compounds of formula XIX in which $R^{14}$ is 4-alkenyl, 2E-alkenyloxy or 3-alkenyloxy, as well as those in which $R^{14}$ is 3E-alkenyl and $X^2$ denotes fluorine or chlorine when $X^1$ stands for fluorine. The preparation of the novel compounds of formulas XI, XII and XIX can be effected according to the methods illustrated in the Synthesis Examples.

If desired, the mixtures in accordance with the invention can also contain dichroic coloring substances, for example azo, azoxy or anthraquinone coloring substances. The amount of coloring substances in the total mixture generally amounts to a maximum of about 10 wt. %.

The preparation of the mixtures in accordance with the invention and the preparation of electro-optical devices can be effected in a manner known per se.

The preparation of the compounds of formula I and of the novel compounds of formulas XI, XII and XIX as well as liquid crystalline mixtures containing these compounds are illustrated further by the following Examples. C is a crystalline phase, S is a smectic phase, $S_B$ is a smectic B phase, N is a nematic phase and I is the isotropic phase. $V_{10}$ denotes the voltage for 10% transmission (direction of view perpendicular to the plate surface). $t_{on}$ and $t_{off}$ denote respectively the switching-on time and the switching-off time and $\Delta n$ denotes the optical anisotropy. $k_{11}$, $k_{22}$ and $k_{33}$ denote the elastic constants for splaying, twisting and bending. $\Delta\epsilon$ denotes the dielectric anisotropy, $\eta$ denotes the bulk viscosity and $\gamma_1$ denotes the rotation viscosity. Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C.), normal pressure is about 1 atmosphere and room temperature is about 23° C. The petroleum ether is a well-known mixture of low-boiling hydrocarbons. Unless indicated otherwise, the examples were carried out as written.

EXAMPLE 1

(a) A suspension of 109.6 g of 4-(4-nitrophenyl)cyclohexanone (preparable by nitrating 4-phenylcyclohexanone) in 1 l of dioxan was treated with 50 ml of triethylamine and 2 g of 5 percent palladium-charcoal and hydrogenated at room temperature and 0.3 bar hydrogen pressure while stirring well. After 2 hours the mixture was filtered. The filtrate was evaporated on a water-jet vacuum at a bath temperature of 30° C. and the evaporation residue was dried at 40° C. overnight in a drying oven under a water-jet vacuum. There were thus obtained 94.5 g of 4-(4-aminophenyl)cyclohexanone as white crystals with m.p. 127°-128° C.

(b) 200 ml of 4N sulfuric acid were heated to 80° C. in a sulfonation flask and then treated with about 5% of a solution of 37.9 g of 4-(4-aminophenyl)cyclohexanone in 200 ml of 4N sulfuric acid. Subsequently, the remaining solution of 4-(4-aminophenyl)cyclohexanone as well as a solution of 15.2 g of sodium nitrite in 45 ml of water were simultaneously added dropwise to the reaction mixture at 80° C. within 1.5 hours. Thereafter, the mixture was treated dropwise at 80° C. within 30 minutes with a solution of 9 g of sodium nitrite in 27 ml of water and stirred at 80° C. for a further 1 hour. After cooling the reaction mixture to 0° C. the separated crystals were removed by filtration under suction, washed with 200 ml of cold water and dried to constant weight at 60° C. in a drying oven under a water-jet vacuum. The crystalline crude product (34.6 g) was suspended in 520 ml of ethyl acetate. The suspension was heated to reflux for 1 hour, treated with 1.7 g of active carbon and then heated to reflux for a further 1 hour. The mixture was subsequently suction filtered (rinsing with 40 ml of warm ethyl acetate) and the filtrate was evaporated under a water-jet vacuum at a bath temperature of 40° C. Drying of the evaporation residue to constant weight at 60° C. in a drying oven under a water-jet vacuum gave 32.2 g of 4-(4-hydroxyphenyl)cyclohexanone as yellow- -brown crystals with m.p. 165°-166° C.

(c) A suspension of 3.8 g of 4-(4-hydroxyphenyl)cyclohexanone in 60 ml of tert.butyl methyl ether was treated in a sulfonation flask under a weak stream of nitrogen with 10.6 g of 2-(1,3-dioxolan-2-yl)ethyl-triphenylphosphonium bromide and 2.2 g of potassium tert.butylate. The mixture was firstly stirred for 30 minutes, then treated portionwise within 2.25 hours at 25° C. with a further 2.7 g of potassium tert.butylate and stirred at room temperature for a further 1 hour. Thereafter, the reaction mixture was treated with an additional 1.8 g of 2-(1,3-dioxolan-2-yl)ethyl-triphenylphosphonium bromide and 0.45 g of potassium tert.butylate and stirred for a further 1 hour. Subsequently, the reaction mixture was poured into 80 ml of water and acidified with 11 ml of 2N sulfuric acid. The aqueous phase was separated and extracted twice with 80 ml of tert.butyl methyl ether each time. The organic phases were washed twice with 50 ml of water each time, dried over sodium sulfate and suction filtered. The filtrate was evaporated to constant weight under a water-jet vacuum at a bath temperature of 40° C. The reddish oil obtained (10.9 g) was separated by chromatography on silica gel with toluene and toluene/tert.butyl methyl ether (vol. 20:1). Evaporation of the product-containing fractions in a water-jet vacuum and drying the residue to constant weight in a drying oven under a water-jet vacuum at 60° C. finally gave 4.5 g of 4-[4-[2-(1,3-dioxolan-2-yl)ethylidene]cyclohexyl]phenol as yellowish crystals with m.p. 125.5°-126.5° C.

(d) A solution of 36.5 g of 4-[4-[2-(1,3-dioxolan-2-yl)ethylidene]cyclohexyl]phenol in 500 ml of toluene and 50 ml of triethylamine was hydrogenated in a hydrogenation autoclave at 90° C. for 1 hour with 3.2 g of 5 percent platinum-charcoal and under 10 bar of hydrogen. The mixture was subsequently suction filtered and the residue was washed with 30 ml of warm toluene. The filtrate was evaporated to constant weight under a water-jet vacuum at a bath temperature of 40° C. The white crystals obtained (37 g) were dissolved in 180 ml of methanol while heating. The solution was left to cool to room temperature and then placed in a refrigerator for 5 hours. The crystals were subsequently removed by filtration under suction, washed with 50 ml of cold methanol and dried at 60° C. in a drying oven under a water-jet vacuum. There were thus obtained 27.6 g of 4-[trans-4-[2-(1,3-dioxolan-2-yl)ethyl]cyclohexyl]phenol as white crystals with m.p. 153.5°-154.5° C.

(e) A mixture of 100 g of 4-[trans-4-[2-(1,3-dioxolan-2-yl)ethyl]cyclohexyl]phenol, 10 g of 5 percent rhodium/aluminium oxide and 1 l of ethyl acetate was hydrogenated in a steel stirring autoclave under 50 bar of hydrogen at 80° C. for 90 minutes. The catalyst was then removed by filtration under suction and washed with 100 ml of ethyl acetate. The filtrate was evaporated and the residue was dried at 25° C./0.4 mbar. There were thus obtained 101.75 g of 4-[trans-4-[2-(1,3-dioxolan-2-yl)ethyl]cyclohexyl] cyclohexanol containing 59% of cis isomer and 36% of trans isomer.

(f) A solution of 12.9 g of pyridinium chlorochromate in 80 ml of methylene chloride was treated dropwise within 5 minutes at room temperature while gassing with nitrogen with a solution of 13.0 g of 4-[trans-4-[2-(1,3-dioxolan-2-yl)ethyl]cyclohexyl]cyclohexanol in 40 ml of methylene chloride. The mixture was stirred for a further 1 hour, then diluted with 100 ml of diethyl ether and filtered and the filtrate was evaporated. The evaporation residue was taken up in 200 ml of diethyl ether, the mixture was filtered, the filtrate was evaporated and then this procedure was repeated twice. Thereafter, the brownish solid mass obtained (12.1 g) was separated by chromatography on silica gel with ethyl acetate/petroleum ether (vol. 1:4). Crystallization of the colorless ketone fraction from 60 ml of ethyl acetate and 200 ml of petroleum ether finally gave 7.0 g of pure 4-[trans-4-[2-(1,3-dioxolan-2-yl)ethyl]cyclohexyl]cyclohexanone; m.p. 100.4° C.

(g) A suspension of 2.97 g of sodium borohydride in 300 ml of isopropanol was treated dropwise at −70° C. while gassing with nitrogen with a solution of 11 g of 4-[trans-4-[2-(1,3-dioxolan-2-yl)ethyl]cyclohexyl]cyclohexanone in 200 ml of isopropanol. After about 1 hour the reaction mixture was left to warm to room temperature, diluted with 500 ml of 0.1N hydrochloric acid and extracted three times with 300 ml of methylene chloride each time. The organic phases were washed with water, dried over magnesium sulfate, filtered and evaporated. Crystallization of the residue (11 g) from 500 ml of ethyl acetate/petroleum ether (vol. 3:5) gave 6.6 g of pure trans-4-[trans-4-[2-(1,3-dioxolan-2-yl)ethyl]cyclohexyl]cyclohexanol with m.p. 129.5° C.

(h) 2.04 g of sodium hydride as an about 50 percent oily suspension were placed in a round flask while gassing with nitrogen and washed twice with pentane. Then, 40 ml of dry tetrahydrofuran and a solution of 6.0 g of trans-4-[trans-4-[2-(1,3-dioxolan-2-yl)ethyl]cyclohexyl]cyclohexanol in 30 ml of tetrahydrofuran were added to the sodium hydride. The mixture was stirred at room temperature for 30 minutes, then treated with 4.0 ml of methyl iodide and heated to reflux for 2 hours. Subsequently, the reaction mixture was cooled, taken up in 200 ml of diethyl ethyl and washed three times with 200 ml of water each time. The organic phase was dried over magnesium sulfate, filtered and evaporated, whereby there were obtained 6.3 g of 2-[2-[trans-4-

(trans-4-methoxycyclohexyl)cyclohexyl]ethyl]-1,3-dioxolane with m.p. 74° C.

(i) 6.2 g of 2-[2-[trans-4-(trans-4-methoxycyclohexyl)cyclohexyl]ethyl]-1,3-dioxolane were treated with 100 ml of water, 50 ml of glacial acetic acid and 20 ml of dioxan while gassing with nitrogen. The mixture was stirred at 100° C. (bath temperature) for 1.5 hours, then neutralized with dilute sodium hydrogen carbonate solution and extracted three times with diethyl ether. The combined ether phases were washed once with water and twice with dilute sodium hydrogen carbonate solution, dried over magnesium sulfate, filtered and evaporated. Recrystallization of the crude aldehyde obtained (4.34 g) from 150 ml of petroleum ether at −20° C. gave 2.8 g of 3-[trans-4-(trans-4-methoxycyclohexyl)cyclohexyl]propionaldehyde in a purity of 96%; m.p. 36° C.

(j) 2.65 g of ethyltriphenylphosphonium bromide were suspended in 40 ml of tert.butyl methyl ether while gassing with argon. The suspension was treated at room temperature with 797 mg of potassium tert.butylate and stirred for 1 hour. The mixture was subsequently cooled to 0° C., treated dropwise within 3 minutes with a solution of 1.1 g of 3-[trans-4-(trans-4-methoxycyclohexyl)cyclohexyl]propionaldehyde in 15 ml of tert.butyl methyl ether and then left to warm slowly to room temperature while stirring. After 2 hours the pale yellow suspension was partitioned between diethyl ether and water. The aqueous phase was separated and washed three times with diethyl ether. The organic phases were washed twice with water, dried over magnesium sulfate, filtered and evaporated. Chromatographic purification of the yellow, solid crude product on silica gel with ethyl acetate/petroleum ether (vol. 3:97) gave 0.91 g of trans-4-(3-pentenyl)-1-(trans-4-methoxycyclohexyl)cyclohexane with a Z/E ratio of 86:11.

(k) 0.91 g of trans-4-(3-pentenyl)-1-(trans-4-methoxycyclohexyl)cyclohexane (Z/E=86:11) was treated with 6 ml of toluene, 0.11 g of sodium benzenesulfinate and 1 ml of 1N hydrochloric acid while gassing with nitrogen. The mixture was stirred at 50° C. for 15 hours, then poured into 100 ml of dilute sodium hydrogen carbonate solution and extracted three times with 50 ml of diethyl ether each time. The combined organic phases were washed with 100 ml of dilute sodium carbonate solution and with 100 ml of water, dried over magnesium sulfate, filtered and evaporated. The yellowish oil obtained (0.9 g) was purified by chromatography on silver nitrate-impregnated silica gel with diethyl ether/hexane (vol. 1:9). Recrystallization of the product obtained (486 mg) from 10 ml of methanol at −20° C. gave pure trans-4-(3E-pentenyl)-1-(trans-4-methoxycyclohexyl)cyclohexane with m.p. (C-N) 16.6° C. and cl.p. (N-I) 43.7° C.

The following compounds can be prepared in an analogous manner:

trans-4-(3-Butenyl)-1-(trans-4-methoxycyclohexyl)cyclohexane, m.p. (C-N) −13.6° C., cl.p. (N-I) 18.0° C.;
trans-4-(3-butenyl)-1-(trans-4-ethoxycyclohexyl)cyclohexane, m.p. (C-N) 13.1° C., cl.p. (N-I) 45.3° C.;
trans-4-(3-butenyl)-1-(trans-4-propyloxycyclohexyl)cyclohexane;
trans-4-(3-butenyl)-1-(trans-4-butyloxycyclohexyl)cyclohexane;
trans-4-(3-butenyl)-1-(trans-4-pentyloxycyclohexyl)cyclohexane;
trans-4-(3-butenyl)-1-(trans-4-hexyloxycyclohexyl)cyclohexane;
trans-4-(3-butenyl)-1-(trans-4-allyloxycyclohexyl)cyclohexane;
trans-4-(3-butenyl)-1-[trans-4-(2E-butenyloxy)cyclohexyl]cyclohexane,
trans-4-(3-butenyl)-1-[trans-4-(2E-pentenyloxy)cyclohexyl]cyclohexane,
trans-4-(3-butenyl)-1-[trans-4-(2E-hexenyloxy)cyclohexyl]cyclohexane,
trans-4-(3-butenyl)-1-[trans-4-(3-butenyloxy)cyclohexyl]cyclohexane,
trans-4-(3-butenyl)-1-[trans-4-(3Z-pentenyloxy)cyclohexyl]cyclohexane,
trans-4-(3-butenyl)-1-[trans-4-(3Z-hexenyloxy)cyclohexyl]cyclohexane,
trans-4-(3E-pentenyl)-1-(trans-4-ethoxycyclohexyl)cyclohexane, m.p. (C-N) 44.5° C., cl.p. (N-I) 76.5° C.;
trans-4-(3E-pentenyl)-1-(trans-4-propyloxycyclohexyl)cyclohexane;
trans-4-(3E-pentenyl)-1-(trans-4-butyloxycyclohexyl)cyclohexane;
trans-4-(3E-pentenyl)-1-(trans-4-pentyloxycyclohexyl)cyclohexane;
trans-4-(3E-pentenyl)-1-(trans-4-hexyloxycyclohexyl)cyclohexane;
trans-4-(3E-pentenyl)-1-(trans-4-allyloxycyclohexyl)cyclohexane;
trans-4-(3E-pentenyl)-1-[trans-4(2E-butenyloxy)cyclohexyl]cyclohexane;
trans-4-(3E-pentenyl)-1-[trans-4-(2E-pentenyloxy)cyclohexyl]cyclohexane;
trans-4-(3E-pentenyl)-1-[trans-4-(2E-hexenyloxy)cyclohexyl]cyclohexane;
trans-4-(3E-pentenyl)-1-[trans-4-(3-butenyloxy)cyclohexyl]cyclohexane;
trans-4-(3E-pentenyl)-1-[trans-4-(3Z-pentenyloxy)cyclohexyl]cyclohexane;
trans-4-(3E-pentenyl)-1-[trans-4-(3Z-hexenyloxy)cyclohexyl]cyclohexane;
trans-4-(3E-hexenyl)-1-(trans-4-methoxycyclohexyl)cyclohexane;
trans-4-(3E-hexenyl)-1-(trans-4-ethoxycyclohexyl)cyclohexane;
trans-4-(3E-hexenyl)-1-(trans-4-propyloxycyclohexyl)cyclohexane;
trans-4-(3E-hexenyl)-1-(trans-4-butyloxycyclohexyl)cyclohexane;
trans-4-(3E-hexenyl)-1-(trans-4-pentyloxycyclohexyl)cyclohexane;
trans-4-(3E-hexenyl)-1-(trans-4-hexyloxycyclohexyl)cyclohexane;
trans-4-(3E-hexenyl)-1-(trans-4-allyloxycyclohexyl)cyclohexane;
trans-4-(3E-hexenyl)-1-[trans-4-(2E-butenyloxy)cyclohexyl]cyclohexane;
trans-4-(3E-hexenyl)-1-[trans-4-(2E-pentenyloxy)cyclohexyl]cyclohexane;
trans-4-(3E-hexenyl)-1-[trans-4-(2E-hexenyloxy)cyclohexyl]cyclohexane;
trans-4-(3E-hexenyl)-1-[trans-4-(3-butenyloxy)cyclohexyl]cyclohexane;
trans-4-(3E-hexenyl)-1-[trans-4-(3Z-pentenyloxy)cyclohexyl]cyclohexane;
trans-4-(3E-hexenyl)-1-[trans-4-(3Z-hexenyloxy)cyclohexyl]cyclohexane.

The following compounds can be prepared in an analogous manner to steps (a) to (i) and further reaction of the propionaldehyde obtained in an analogous manner to Example 2, steps (h), (i) and (j):

trans-4-(4-Pentenyl)-1-(trans-4-methoxycyclohexyl)cyclohexane, m.p. (C-S$_B$) 7.7° C., cl.p. (S$_B$-I) 14.0° C.;
trans-4-(4-pentenyl)-1-(trans-4-ethoxycyclohexyl)cyclohexane, m.p. (C-S$_B$) 10.5° C., cl.p. (S$_B$-I) 43.1° C.;
trans-4-(4-pentenyl)-1-(trans-4-propyloxycyclohexyl)cyclohexane;
trans-4-(4-pentenyl)-1-(trans-4-butyloxycyclohexyl)cyclohexane;
trans-4-(4-pentenyl)-1-(trans-4-pentyloxycyclohexyl)cyclohexane;
trans-4-(4-pentenyl)-1-(trans-4-hexyloxycyclohexyl)cyclohexane;
trans-4-(4-pentenyl)-1-(trans-4-allyloxycyclohexyl)cyclohexane;
trans-4-(4-pentenyl)-1-[trans-4-(3-butenyloxy)cyclohexyl]cyclohexane;
trans-4-(4Z-hexenyl)-1-(trans-4-methoxycyclohexyl)cyclohexane;
trans-4-(4Z-hexenyl)-1-(trans-4-ethoxycyclohexyl)cyclohexane;
trans-4-(4Z-hexenyl)-1-(trans-4-propyloxycyclohexyl)cyclohexane;
trans-4-(4Z-hexenyl)-1-(trans-4-butyloxycyclohexyl)cyclohexane;
trans-4-(4Z-hexenyl)-1-(trans-4-pentyloxycyclohexyl)cyclohexane;
trans-4-(4Z-hexenyl)-1-(trans-4-hexyloxycyclohexyl)cyclohexane;
trans-4-(4Z-hexenyl)-1-(trans-4-allyloxycyclohexyl)cyclohexane;
trans-4-(4Z-hexenyl)-1-[trans-4-(3-butenyloxy)cyclohexyl]cyclohexane.

The following compounds can be prepared by reacting the 4-(4-hydroxyphenyl)cyclohexanone (step b) in an analogous manner to Example 2, steps (h) and (i), acetalizing the resulting 4-(trans-4-formylcyclohexyl)phenol obtained with ethylene glycol in the presence of p-toluenesulfonic acid and further reacting the dioxolane in an analogous manner to the previous steps (e) to (k):

trans-4-Vinyl-1-(trans-4-methoxycyclohexyl)cyclohexane;
trans-4-vinyl-1-(trans-4-ethoxycyclohexyl)cyclohexane;
trans-4-vinyl-1-(trans-4-propyloxycyclohexyl)cyclohexane;
trans-4-vinyl-1-(trans-4-butyloxycyclohexyl)cyclohexane;
trans-4-vinyl-1-(trans-4-pentyloxycyclohexyl)cyclohexane;
trans-4-vinyl-1-(trans-4-hexyloxycyclohexyl)cyclohexane;
trans-4-vinyl-1-(trans-4-allyloxycyclohexyl)cyclohexane;
trans-4-vinyl-1-[trans-4-(3-butenyloxy)cyclohexyl]cyclohexane;
trans-4-(1E-propenyl)-1-(trans-4-methoxycyclohexyl)cyclohexane, m.p. <-20° C., cl.p. (N-I) 15° C.;
trans-4-(1E-propenyl)-1-(trans-4-ethoxycyclohexyl)cyclohexane;
trans-4-(1E-propenyl)-1-(trans-4-propyloxycyclohexyl)cyclohexane;
trans-4-(1E-propenyl)-1-(trans-4-butyloxycyclohexyl)cyclohexane;
trans-4-(1E-propenyl)-1-(trans-4-pentyloxycyclohexyl)cyclohexane;
trans-4-(1E-propenyl)-1-(trans-4-hexyloxycyclohexyl)cyclohexane;
trans-4-(1E-propenyl)-1-(trans-4-allyloxycyclohexyl)cyclohexane;
trans-4-(1E-propenyl)-1-[trans-4-(3-butenyloxy)cyclohexyl]cyclohexane;
trans-4-(1E-butenyl)-1-(trans-4-methoxycyclohexyl)cyclohexane;
trans-4-(1E-butenyl)-1-(trans-4-ethoxycyclohexyl)cyclohexane;
trans-4-(1E-butenyl)-1-(trans-4-propyloxycyclohexyl)cyclohexane;
trans-4-(1E-butenyl)-1-(trans-4-butyloxycyclohexyl)cyclohexane;
trans-4-(1E-butenyl)-1-(trans-4-pentyloxycyclohexyl)cyclohexane;
trans-4-(1E-butenyl)-1-(trans-4-allyloxycyclohexyl)cyclohexane;
trans-4-(1E-butenyl)-1-[trans-4-(3-butenyloxycyclohexyl)]cyclohexane;
trans-4-(1E-pentenyl)-1-(trans-4-methoxycyclohexyl)cyclohexane;
trans-4-(1E-pentenyl)-1-(trans-4-ethoxycyclohexyl)cyclohexane;
trans-4-(1E-pentenyl)-1-(trans-4-propyloxycyclohexyl)cyclohexane;
trans-4-(1E-pentenyl)-1-(trans-4-butyloxycyclohexyl)cyclohexane;
trans-4-(1E-pentenyl)-1-(trans-4-allyloxycyclohexyl)cyclohexane;
trans-4-(1E-pentenyl)-1-[trans-4-(3-butenyloxy)cyclohexyl]cyclohexane.

The following compounds can also be prepared according to the above methods starting from 4-(2-phenylehtyl)cyclohexanone [preparable in an analogous manner to the nitrile described in Mol. Cryst. Liq. Cryst. 131, 327 (1985)]:

4-[2-[trans-4-(2-(1,3-Dioxolan-2-yl)ethyl)cyclohexyl]ethyl]cyclohexanone;
trans-4-(3-butenyl)-1-[2-(trans-4-methoxycyclohexyl)ethyl]cyclohexane;
trans-4-(3-butenyl)-1-[2-(trans-4-ethoxycyclohexyl)ethyl]cyclohexane;
trans-4-(3-butenyl)-1-[2-(trans-4-propyloxycyclohexyl)ethyl]cyclohexane;
trans-4-(3-butenyl)-1-[2-(trans-4-butyloxycyclohexyl)ethyl]cyclohexane;
trans-4-(3-butenyl)-1-[2-(trans-4-pentyloxycyclohexyl)ethyl]cyclohexane;
trans-4-(3-butenyl)-1-[2-(trans-4-hexyloxycyclohexyl)ethyl]cyclohexane;
trans-4-(3-butenyl)-1-[2-(trans-4-allyloxycyclohexyl)ethyl]cyclohexane;
trans-4-(3-butenyl)-1-[2-(trans-4-(2E-butenyloxy)cyclohexyl)ethyl]cyclohexane;
trans-4-(3-butenyl)-1-[2-(trans-4-(2E-pentyloxy)cyclohexyl)ethyl]cyclohexane;
trans-4-(3-butenyl)-1-[2-(trans-4-(2E-hexenyloxy)cyclohexyl)ethyl]cyclohexane;
trans-4-(3-butenyl)-1-[2-(trans-4-(3-butenyloxy)cyclohexyl)ethyl]cyclohexane;
trans-4-(3-butenyl)-1-[2-(trans-4-(3Z-pentyloxy)cyclohexyl)ethyl]cyclohexane;
trans-4-(3-butenyl)-1-[2-(trans-4-(3Z-hexenyloxy)cyclohexyl)ethyl]cyclohexane;
trans-4-(3E-pentenyl)-1-[2-(trans-4-methoxycyclohexyl)ethyl]cyclohexane;

trans-4-(3E-pentenyl)-1-[2-(trans-4-ethoxycyclohexyl)ethyl]cyclohexane;
trans-4-(3E-pentenyl)-1-[2-(trans-4-propyloxycyclohexyl)ethyl]cyclohexane;
trans-4-(3E-pentenyl)-1-[2-(trans-4-butyloxycyclohexyl)ethyl]cyclohexane;
trans-4-(3E-pentenyl)-1-[2-(trans-4-pentyloxycyclohexyl)ethyl]cyclohexane;
trans-4-(3E-pentenyl)-1-[2-(trans-4-hexyloxycyclohexyl)ethyl]cyclohexane;
trans-4-(3E-pentenyl)-1-[2-(trans-4-allyloxycyclohexyl)ethyl]cyclohexane;
trans-4-(3E-pentenyl)-1-[2-(trans-4-(2E-butenyloxy)cyclohexyl)ethyl]cyclohexane;
trans-4-(3E-pentenyl)-1-[2-(trans-4-(2E-pentenyloxy)cyclohexyl)ethyl]cyclohexane;
trans-4-(3E-pentenyl)-1-[2-(trans-4-(2E-hexenyloxy)cyclohexyl)ethyl]cyclohexane;
trans-4-(3E-pentenyl)-1-[2-(trans-4-(3-butenyloxy)cyclohexyl)ethyl]cyclohexane;
trans-4-(3E-pentenyl)-1-[2-(trans-4-(3Z-pentenyloxy)cyclohexyl)ethyl]cyclohexane;
trans-4-(3E-pentenyl)-1-[2-(trans-4-(3Z-hexenyloxy)cyclohexyl)ethyl]cyclohexane;
trans-4-(3E-hexenyl)-1-[2-(trans-4-methoxycyclohexyl)ethyl]cyclohexane;
trans-4-(3E-hexenyl)-1-[2-(trans-4-ethoxycyclohexyl)ethyl]cyclohexane;
trans-4-(3E-hexenyl)-1-[2-(trans-4-propyloxycyclohexyl)ethyl]cyclohexane;
trans-4-(3E-hexenyl)-1-[2-(trans-4-butyloxycylohexyl)ethyl]cyclohexane;
trans-4-(3E-hexenyl)-1-[2-(trans-4-pentyloxycyclohexyl)ethyl]cyclohexane;
trans-4-(3E-hexenyl)-1-[2-(trans-4-hexyloxycyclohexyl)ethyl]cyclohexane;
trans-4-(3E-hexenyl)-1-[2-(trans-4-allyloxycyclohexyl)ethyl]cyclohexane;
trans-4-(3E-hexenyl)-1-[2-(trans-4-(3-butenyloxy)cyclohexyl)ethyl]cyclohexane;
trans-4-(4-pentenyl)-1-[2-(trans-4-methoxycyclohexyl)ethyl]cyclohexane;
trans-4-(4-pentenyl)-1-[2-(trans-4-ethoxycyclohexyl)ethyl]cyclohexane;
trans-4-(4-pentenyl)-1-[2-(trans-4-propyloxycyclohexyl)ethyl]cyclohexane;
trans-4-(4-pentenyl)-1-[2-(trans-4-butyloxycyclohexyl)ethyl]cyclohexane;
trans-4-(4-pentenyl)-1-[2-(trans-4-pentyloxycyclohexyl)ethyl]cyclohexane;
trans-4-(4-pentenyl)-1-[2-(trans-4-hexyloxycyclohexyl)ethyl]cyclohexane;
trans-4-(4-pentenyl)-1-[2-(trans-4-allyloxycyclohexyl)ethyl]cyclohexane;
trans-4-(4-pentenyl)-1-[2-(trans-4-(3-butenyloxy)cyclohexyl)ethyl]cyclohexane;
trans-4-(4Z-hexenyl)-1-[2-(trans-4-methoxycyclohexyl)ethyl]cyclohexane;
trans-4-(4Z-hexenyl)-1-[2-(trans-4-ethoxycyclohexyl)ethyl]cyclohexane;
trans-4-(4Z-hexenyl)-1-[2-(trans-4-propyloxycyclohexyl)ethyl]cyclohexane;
trans-4-(4Z-hexenyl)-1-[2-(trans-4-butyloxycyclohexyl)ethyl]cyclohexane;
trans-4-(4Z-hexenyl)-1-[2-(trans-4-allyloxycyclohexyl)ethyl]cyclohexane;
trans-4-(4Z-hexenyl)-1-[2-(trans-4-(3-butenyloxy)cyclohexyl)ethyl]cyclohexane;
trans-4-vinyl-1-[2-(trans-4-methoxycyclohexyl)ethyl]cyclohexane;
trans-4-vinyl-1-[2-(trans-4-ethoxycyclohexyl)ethyl]cyclohexane;
trans-4-vinyl-1-[2-(trans-4-propyloxycyclohexyl)ethyl]cyclohexane;
trans-4-vinyl-1-[2-(trans-4-butyloxycyclohexyl)ethyl]cyclohexane;
trans-4-vinyl-1-[2-(trans-4-pentyloxycyclohexyl)ethyl]cyclohexane;
trans-4-vinyl-1-[2-(trans-4-hexyloxycyclohexyl)ethyl]cyclohexane;
trans-4-vinyl-1-[2-(trans-4-allyloxycyclohexyl)ethyl]cyclohexane;
trans-4-vinyl-1-[2-(trans-4-(3-butenyloxy)cyclohexyl)ethyl]cyclohexane;
trans-4-(1E-propenyl)-1-[2-(trans-4-methoxycyclohexyl)ethyl]cyclohexane;
trans-4-(1E-propenyl)-1-[2-(trans-4-ethoxycyclohexyl)ethyl]cyclohexane;
trans-4-(1E-propenyl)-1-[2-(trans-4-propyloxycyclohexyl)ethyl]cyclohexane;
trans-4-(1E-propenyl)-1-[2-(trans-4-butyloxycyclohexyl)ethyl]cyclohexane;
trans-4-(1E-propenyl)-1-[2-(trans-4-pentyloxycyclohexyl)ethyl]cyclohexane;
trans-4-(1E-propenyl)-1-[2-(trans-4-hexyloxycyclohexyl)ethyl]cyclohexane;
trans-4-(1E-propenyl)-1-[2-(trans-4-allyloxycyclohexyl)ethyl]cyclohexane;
trans-4-(1E-propenyl)-1-[2-(trans-4-(3-butenyloxy)cyclohexyl)ethyl]cyclohexane;
trans-4-(1E-butenyl)-1-[2-(trans-4-methoxycyclohexyl)ethyl]cyclohexane;
trans-4-(1E-butenyl)-1-[2-(trans-4-ethoxycyclohexyl)ethyl]cyclohexane;
trans-4-(1E-butenyl)-1-[2-(trans-4-propyloxycyclohexyl)ethyl]cyclohexane;
trans-4-(1E-butenyl)-1-[2-(trans-4-butyloxycyclohexyl)ethyl]cyclohexane;
trans-4-(1E-butenyl)-1-[2-(trans-4-pentyloxycyclohexyl)ethyl]cyclohexane;
trans-4-(1E-butenyl)-1-[2-(trans-4-allyloxycyclohexyl)ethyl]cyclohexane;
trans-4-(1E-butenyl)-1-[2-(trans-4-(3-butenyloxy)cyclohexyl)ethyl]cyclohexane;
trans-4-(1E-pentenyl)-1-[2-(trans-4-methoxycyclohexyl)ethyl]cyclohexane;
trans-4-(1E-pentenyl)-1-[2-(trans-4-ethoxycyclohexyl)ethyl]cyclohexane;
trans-4-(1E-pentenyl)-1-[2-(trans-4-propyloxycyclohexyl)ethyl]cyclohexane;
trans-4-(1E-pentenyl)-1-[2-(trans-4-butyloxycyclohexyl)ethyl]cyclohexane;
trans-4-(1E-pentenyl)-1-[2-(trans-4-allyloxycyclohexyl)ethyl]cyclohexane;
trans-4-(1E-pentenyl)-1-[2-(trans-4-(3-butenyloxy)cyclohexyl)ethyl]cyclohexane.

EXAMPLE 2

(a) 140.9 g of 2-(1,3-dioxolan-2-yl)ethyl-triphenylphosphonium bromide were suspended in 4.5 l of tetrahydrofuran while gassing with nitrogen and the suspension was treated at 0° C. within 5 minutes with 36.8 g of potassium tert.butylate. The orange suspension was stirred at room temperature for a further 1 hour and treated within 5 minutes with 46.1 g of 4-(4-oxocyclohexyl)benzamide. The reaction mixture was stirred at room temperature for a further 4.5 hours and then concentrated in a vacuum. The yellowish crystals obtained (212.5 g) were treated with 1.2 l of diethyl ether. The mixture was stirred at room temperature for 30 minutes and then suction filtered. The residue was washed with diethyl ether and then suspended in 700 ml of water. The mixture was stirred for 15 minutes and then suction filtered. The residue was washed with water and dissolved while heating in 600 ml of dioxan. The solution was left to cool to room temperature. The separated crystals were removed by filtration under suction, washed with a small amount of dioxan and hexane and dried at 60° C. in a vacuum, whereby there were obtained 39.2 g of crystalline 4-[4-[2-(1,3-dioxolan-2-yl)ethylidene]cyclohexyl]benzamide with m.p. 209°–212° C. Working-up of the mother liquor (72.6 g) gave a further 7.7 g of product and 64.2 g of a second mother liquor.

(b) A mixture of 500 mg of 4-[4-[2-(1,3-dioxolan-2-yl)ethylidene]cyclohexyl]benzamide and 20 ml of dioxan/triethylamine (vol. 9:1) was hydrogenated in the presence of 500 mg of 10 percent platinum-charcoal for 2 hours. The reaction mixture was then filtered and the filtrate was evaporated. Recrystallization of the evaporation residue from 40 ml of dioxan gave 230 mg of 4-[trans-4-[2-(1,3-dioxolan-2-yl)ethyl]cyclohexyl]benzamide as colorless crystals.

(c) 27 g of 4-[trans-4-[2-(1,3-dioxolan-2-yl)ethyl]cyclohexyl]benzamide were hydrogenated for 8 hours using 5 g of 5 percent ruthenium-charcoal in dioxan at 120° C. and 40 bar hydrogen. The crude product (25 g) obtained after filtration and washing with tetrahydrofuran contained 69% of the cis isomer and 25% of the trans isomer of 4-[trans-4-[2-(1,3-dioxolan-2-yl)ethyl]cyclohexyl]cyclohexanecarboxamide.

(d) 42 g of crude 4-[trans-4-[2-(1,3-dioxolan-2-yl)ethyl]cyclohexyl]cyclohexanecarboxamide were suspended in 500 ml of ethylene glycol while gassing with argon and then treated with 19 g of solid potassium hydroxide. The mixture was heated to 180° C. (bath temperature) for 5 hours while stirring. After cooling the reaction mixture was poured into 500 ml of water, acidified to pH about 3 with 10 percent hydrochloric acid and extracted three times with 300 ml of methylene chloride each time. The combined organic phases were washed once with 500 ml of 1 percent hydrochloric acid and twice with 500 ml of water each time, dried over magnesium sulfate, filtered and evaporated. The dark brown crude product (41 g) was purified by chromatography on silica gel with ethyl acetate. Crystallization of the product obtained (36 g) from acetone gave 13.8 g of pure trans-4-[trans-4-(2-(1,3-dioxolan-2-yl)ethyl]cyclohexyl]cyclohexanecarboxylic acid. Working-up of the mother liquor gave a further 2.5 g of pure product.

(e) 18 g of trans-4-[trans-4-(2-(1,3-dioxolan-2-yl)ethyl]cyclohexyl]cyclohexanecarboxylic acid were dissolved in 600 ml of chloroform while gassing with argon and the solution was treated dropwise at 0° C. while stirring within 3 minutes with a solution of 7.2 ml of ethyl chloroformate in 40 ml of chloroform. The reaction solution was stirred for a further 30 minutes. Ammonia gas was then conducted into the solution during 10 minutes. The mixture was stirred at 0° C. for a further 30 minutes and then extracted twice with 300 ml of water each time. The aqueous phases were back-extracted with in each case 100 ml of chloroform. The combined organic phases were dried over magnesium sulfate, filtered and evaporated. Recrystallization of the brown crystalline crude product obtained (19 g) from 800 ml of methylene chloride gave 13 g of trans-4-[trans-4-[2-(1,3-dioxolan-2-yl)ethyl]cyclohexyl]cyclohexanecarboxamide as pale brown crystals.

(f) 2.1 g of trans-4-[trans-4-[2-(1,3-dioxolan-2-yl)ethyl]cyclohexyl]cyclohexanecarboxamide were suspended in 60 ml of dimethylformamide while gassing with argon. The suspension was treated with 1.32 ml of pyridine and 0.898 ml of methanesulfochloride and stirred at 60° C. (bath temperature) for 1.5 hours. The reaction solution was subsequently partitioned between methylene chloride and 10 percent hydrochloric acid. The aqueous phase was extracted twice with 100 ml of methylene chloride each time. The organic phases were washed twice with 100 ml of water each time, dried over magnesium sulfate, filtered and concentrated. There were thus obtained 2.5 g of trans-4-[trans-4-[2-(1,3-dioxolan-2-yl)ethyl]cyclohexyl]cyclohexanecarbonitrile as yellow crystals in a purity of 96%.

(g) 3.0 g of crude trans-4-[trans-4-[2-(1,3-dioxolan-2-yl)ethyl]cyclohexyl]cyclohexanecarbonitrile were suspended in 50 ml of water, 25 ml of glacial acetic acid and 10 ml of dioxan while gassing with argon and stirred at 100° C. for 1 hour. Thereafter, the reaction solution was treated with 100 ml of water. The aqueous phase was separated and extracted three times with 100 ml of diethyl ether each time. The organic phases were washed with 100 ml of dilute sodium hydrogen carbonate solution and with 100 ml of water, dried over magnesium sulfate, filtered and concentrated. Recrystallization of the yellow crystals obtained (2.25 g) from 60 ml of hexane gave 1.98 g of 3-[trans-4-(trans-4-cyanocyclohexyl)cyclohexyl]propionaldehyde as colorless crystals.

(h) 4.11 g of methoxymethyl-triphenylphosphonium chloride were suspended in 60 ml of tert.butyl methyl ether while gassing with argon and treated at room temperature within 2 minutes with 1.26 g of potassium tert.butylate. The suspension was stirred at room temperature for a further 1 hour, then cooled to 0° C. and treated dropwise within 5 minutes with a solution of 1.98 g of 3-[trans-4-(trans-4-cyanocyclohexyl)cyclohexyl]propionaldehyde in 25 ml of tert.butyl methyl ether. The reaction mixture was stirred at 0° C. for a further 45 minutes, then diluted with 100 ml of water and extracted three times with 100 ml of diethyl ether each time. The organic phases were washed twice with 100 ml of water each time, dried over magnesium sulfate, filtered and concentrated. Chromatographic purification of the crude product (5.1 g) on silica gel at 0.5 bar with ethyl acetate/petroleum ether (vol. 5:95) gave 2.0 g of trans-4-[trans-4-(4-methoxy-3-butenyl)cyclohexyl]cyclohexanecarbonitrile as a colorless milky oil.

(i) 1.65 g of trans-4-[trans-4-(4-methoxy-3-butenyl)cyclohexyl]cyclohexanecarbonitrile were suspended in 50 ml of water, 25 ml of glacial acetic acid and 12 ml of dioxan while gassing with argon. The suspension was stirred at 80° C. (bath temperature) for 2 hours and then diluted with 50 ml of water. The aqueous phase was separated and extracted three times with 100 ml of diethyl ether each time. The organic phases were washed twice with 100 ml of water each time, then with 100 ml of saturated sodium hydrogen carbonate solution and again with 100 ml of water, then dried over magnesium sulfate, filtered and concentrated. There were thus obtained 1.5 g of 4-[trans-4-(trans-4-cyanocyclohexyl)cyclohexyl]butyraldehyde as colorless crystals.

(j) 3.28 g of methyltriphenylphosphonium bromide were suspended in 40 ml of tert.butyl methyl ether while gassing with argon. The suspension was treated at room temperature within 1 minute with 962 mg of potassium tert.butylate and stirred for 1 hour. The mixture was subsequently cooled to 0° C., treated dropwise within 3 minutes with a solution of 1.5 g of 4-[trans-4-(trans-4-cyanocyclohexyl)cyclohexyl]butyraldehyde in 20 ml of tert.butyl methyl ether and stirred at 0° C. for a further 45 minutes. Thereafter, the reaction mixture was diluted with 80 ml of water and extracted three times with 100 ml of petroleum ether each time. The organic phases were washed twice with 100 ml of water each time, dried over magnesium sulfate, filtered and concentrated. Chromatographic purification of the crude product (2.1 g) on silica gel at 0.5 bar with ethyl acetate/petroleum ether (vol. 2:98) and recrystallization from 20 ml of methanol gave 1.26 g of trans-4-[trans-4-(4-pentenyl)cyclohexyl]cyclohexanecarbonitrile as colorless crystals with m.p. (C-$S_B$) 20.1° C., $S_B$-N 36.9° C., cl.p. (N-I) 54.8° C.

The following compounds can be prepared in an analogous manner:

trans-4-[trans-4-(4Z-Hexenyl)cyclohexyl]cyclohexanecarbonitrile;
trans-4-[trans-4-(4Z-heptenyl)cyclohexyl]cyclohexanecarbontrile;
trans-4-[trans-4-(4Z-octenyl)cyclohexyl]cyclohexanecarbonitrile;
trans-4-[trans-4-(4Z-nonenyl)cyclohexyl]cyclohexanecarbonitrile;
trans-4-[trans-4-(4Z-decenyl)cyclohexyl]cyclohexanecarbonitrile.

The following compounds can be prepared by reacting the 3-[trans-4-(trans-4-cyanocyclohexyl)cyclohexyl]propionaldehyde obtained in step (g) in an analogous manner to step (j) and optional E/Z isomerization in an analogous manner to Example 1k):

trans-4-[trans-4-(3-Butenyl)cyclohexyl]cyclohexanecarbonitrile; m.p. (C-N) 50.7° C., cl.p. (N-I) 82.7° C.;
trans-4-[trans-4-(3E-pentenyl)cyclohexyl]cyclohexanecarbonitrile; m.p. (C-N) 79.4° C., cl.p. (N-I) 99.5° C.;
trans-4-[trans-4-(3E-hexenyl)cyclohexyl]cyclohexanecarbonitrile;
trans-4-[trans-4-(3E-heptenyl)cyclohexyl]cyclohexanecarbonitrile;
trans-4-[trans-4-(3E-octenyl)cyclohexyl]cyclohexanecarbonitrile;
trans-4-[trans-4-(3E-nonenyl)cyclohexyl]cyclohexanecarbonitrile;
trans-4-[trans-4-(3E-decenyl)cyclohexyl]cyclohexanecarbonitrile.

The following compounds can be prepared by reacting the 4-(4-oxocyclohexyl)benzamide in an analogous manner to steps (h) and (i), acetalizing the 4-(trans-4-formylcyclohexyl)benzamide, obtained by crystallization, with ethylene glycol in the presence of p-toluenesulfonic acid, further reaction of the dioxolane in an analogous manner to steps (c) to (g), subsequent Wittig reaction in an analogous manner to step (j) and optional E/Z isomerization in an analogous manner to Example 1k):

trans-4-(trans-4-Vinylcyclohexyl)cyclohexanecarbonitrile, m.p. (C-N) 55.7° C., cl.p. (N-I) 59° C.;
trans-4-[trans-4-(1E-propenyl)cyclohexyl]cyclohexanecarbonitrile, m.p. (C-N) 64.9° C., cl.p. (N-I) 100.1° C.;
trans-4-[trans-4-(1E-butenyl)cyclohexyl]cyclohexanecarbonitrile, m.p. (C-S) 38.5° C., phase transition (S-N) 59° C., cl.p. (N-I) 91° C.;
trans-4-[trans-4-(1E-pentenyl)cyclohexyl]cyclohexanecarbonitrile, m.p. (C-N) 59.3° C., cl.p. (N-I) 91.7° C.;
trans-4-[trans-4-(1E-hexenyl)cyclohexyl]cyclohexanecarbonitrile;
trans-4-[trans-4-(1E-heptenyl)cyclohexyl]cyclohexanecarbonitrile;
trans-4-[trans-4-(1E-octenyl)cyclohexyl]cyclohexanecarbonitrile;
trans-4-[trans-4-(1E-nonenyl)cyclohexyl]cyclohexanecarbonitrile;
trans-4-[trans-4-(1E-decenyl)cyclohexyl]cyclohexanecarbonitrile.

The following compounds can also be prepared starting from 4-[2-(4-oxocyclohexyl)ethyl]benzamide [preparable from the nitrile described in Mol. Cryst. Liq. Cryst. 131, 327 (1985)] in an analogous manner to the above method:

trans-4-[2-(trans-4-(4-Pentenyl)cyclohexyl)ethyl]cyclohexanecarbonitrile;
trans-4-[2-(trans-4-(4Z-hexenyl)cyclohexyl)ethyl]cyclohexanecarbonitrile;
trans-4-[2-(trans-4-(4Z-heptenyl)cyclohexyl)ethyl]cyclohexanecarbonitrile;
trans-4-[2-(trans-4-(4Z-octenyl)cyclohexyl)ethyl]cyclohexanecarbonitrile;
trans-4-[2-(trans-4-(4Z-nonenyl)cyclohexyl)ethyl]cyclohexanecarbonitrile;
trans-4-[2-(trans-4-(4Z-decenyl)cyclohexyl)ethyl]cyclohexanecarbonitrile;
trans-4-[2-(trans-4-(3-butenyl)cyclohexyl)ethyl]cyclohexanecarbonitrile;
trans-4-[2-(trans-4-(3E-pentenyl)cyclohexyl)ethyl]cyclohexanecarbonitrile;
trans-4-[2-(trans-4-(3E-hexenyl)cyclohexyl)ethyl]cyclohexanecarbonitrile;
trans-4-[2-(trans-4-(3E-heptenyl)cyclohexyl)ethyl]cyclohexanecarbonitrile;
trans-4-[2-(trans-4-(3E-octenyl)cyclohexyl)ethyl]cyclohexanecarbonitrile;
trans-4-[2-(trans-4-(3E-nonenyl)cyclohexyl)ethyl]cyclohexanecarbonitrile;
trans-4-[2-(trans-4-(3E-decenyl)cyclohexyl)ethyl]cyclohexanecarbonitrile;
trans-4-[2-(trans-4-vinylcyclohexyl)ethyl]cyclohexanecarbonitrile;
trans-4-[2-(trans-4-(1E-propenyl)cyclohexyl)ethyl]cyclohexanecarbonitrile;
trans-4-[2-(trans-4-(1E-butenyl)cyclohexyl)ethyl]cyclohexanecarbonitrile;
trans-4-[2-(trans-4-(1E-pentenyl)cyclohexyl)ethyl]cyclohexanecarbonitrile;
trans-4-[2-(trans-4-(1E-hexenyl)cyclohexyl)ethyl]cyclohexanecarbonitrile;
trans-4-[2-(trans-4-(1E-heptenyl)cyclohexyl)ethyl]cyclohexanecarbonitrile;
trans-4-[2-(trans-4-(1E-octenyl)cyclohexyl)ethyl]cyclohexanecarbonitrile;
trans-4-[2-(trans-4-(1E-nonenyl)cyclohexyl)ethyl]cyclohexanecarbonitrile;
trans-4-[2-(trans-4-(1E-decenyl)cyclohexyl)ethyl]cyclohexanecarbonitrile.

EXAMPLE 3

(a) A solution of 1.71 g of trans-4-[trans-4-(4-pentenyl)cyclohexyl]cyclohexanecarbonitrile (prepared according to Example 2) in 30 ml of diethylene glycol was treated with 3.11 g of potassium hydroxide and stirred at 130° C. for 3 hours. The mixture was then poured on to ice-water, acidified with 25 percent hydrochloric acid and extracted three times with diethyl ether. The organic phases were combined, washed three times with water, dried over magnesium sulfate and evaporated. Recrystallization of the brown, crystalline residue (1.74 g) from 30 ml of hexane gave 996 mg of trans-4-[trans-4-(4-pentenyl)cyclohexyl]cyclohexanecarboxylic acid as yellowish crystals.

(b) A solution of 996 mg of trans-4-[trans-4-(4-pentenyl)cyclohexyl]cyclohexanecarboxylic acid in 80 ml of methylene chloride was treated with 752 mg of p-fluorophenol, 61 mg of 4-(dimethylamino)pyridine and 1.03 g of dicyclohexylcarbodiimide and stirred at room temperature for 15 hours. The reaction mixture was subsequently filtered. The filtrate was evaporated and the residue obtained was purified by chromatography on silica gel with ethyl acetate/petroleum ether (vol. 3:97). Crystallization of the product obtained (1.24 g) from 40 ml of hexane gave 757 mg of pure trans-4-[trans-4-(4-pentenyl)cyclohexyl]cyclohexanecarboxylic acid 4-fluorophenyl ester with m.p. (C-N) 70.3° C. and cl.p. (N-I) 158.7° C.

The following compounds can be prepared in an analogous manner:

trans-4-(4-Pentenyl)cyclohexanecarboxylic acid 4-fluorophenyl ester, m.p. 31.3° C.;
trans-4-(4-pentenyl)cyclohexanecarboxylic acid 3,4-difluorophenyl ester, m.p. 12.4° C.;
trans-4-(4-pentenyl)cyclohexanecarboxylic acid 4-chlorophenyl ester;
4-(3-butenyloxy)benzoic acid 4-fluorophenyl ester, m.p. 65° C.;
4-(3-butenyloxy)benzoic acid 3,4-difluorophenyl ester, m.p. 47.5° C.;
4-(3-butenyloxy)benzoic acid 4-chlorophenyl ester;
trans-4-[trans-4-(4-pentenyl)cyclohexyl]cyclohexanecarboxylic acid 3,4-difluorophenyl ester;
trans-4-[trans-4-(4-pentenyl)cyclohexyl]cyclohexanecarboxylic acid 4-chlorophenyl ester;
trans-4-[trans-4-(4-pentenyl)cyclohexyl]cyclohexanecarboxylic acid 3-chloro-4-fluorophenyl ester;
trans-4-[trans-4-(4-pentenyl)cyclohexyl]cyclohexanecarboxylic acid 3-fluoro-4-chlorophenyl ester;
4-[trans-4-(4-pentenyl)cyclohexyl]benzoic acid 4-fluorophenyl ester;
4-[trans-4-(4-pentenyl)cyclohexyl]benzoic acid 3,4-difluorophenyl ester;
5-[trans-4-(4-pentenyl)cyclohexyl]-2-pyrimidinecarboxylic acid 4-fluorophenyl ester;
2-[trans-4-(4-pentenyl)cyclohexyl]-5-pyrimidinecarboxylic acid 4-fluorophenyl ester;
4-[5-(4-pentenyl)-2-pyrimidinyl]benzoic acid 4-fluorophenyl ester;
4-[2-(4-pentenyl)-5-pyrimidinyl]benzoic acid 4-fluorophenyl ester;
trans-4-(4Z-hexenyl)cyclohexanecarboxylic acid 4-fluorophenyl ester;
trans-4-(4Z-hexenyl)cyclohexanecarboxylic acid 3,4-difluorophenyl ester;
4-(3Z-pentenyloxy)benzoic acid 4-fluorophenyl ester;
trans-4-[trans-4-(4Z-hexenyl)cyclohexyl]cyclohexanecarboxylic acid 4-fluorophenyl ester;
4-[trans-4-(4Z-hexenyl)cyclohexyl]benzoic acid 4-fluorophenyl ester;
trans-4-(3-butenyl)cyclohexanecarboxylic acid 3,4-difluorophenyl ester, m.p. 42.0° C.;
trans-4-(3-butenyl)cyclohexanecarboxylic acid 4-chlorophenyl ester;
4-allyloxybenzoic acid 4-fluorophenyl ester;
4-allyloxybenzoic acid 3,4-difluorophenyl ester;
4-allyloxybenzoic acid 4-chlorophenyl ester;
trans-4-[trans-4-(3-butenyl)cyclohexyl]cyclohexanecarboxylic acid 3,4-difluorophenyl ester, m.p. (C-N) 55.1° C., cl.p. (N-I) 153.6° C.;
trans-4-[trans-4-(3-butenyl)cyclohexyl]cyclohexanecarboxylic acid 4-chlorophenyl ester, m.p. (C-N) 78.3° C., cl.p. (N-I) 213.5° C.;
trans-4-[trans-4-(3-butenyl)cyclohexyl]cyclohexanecarboxylic acid 3-chloro-4-fluorophenyl ester;
trans-4-[trans-4-(3-butenyl)cyclohexyl]cyclohexanecarboxylic acid 3-fluoro-4-chlorophenyl ester;
4-[trans-4-(3-butenyl)cyclohexyl]benzoic acid 3,4-difluorophenyl ester;
trans-4-(3E-pentenyl)cyclohexanecarboxylic acid 3,4-difluorophenyl ester;
4-(2E-butenyloxy)benzoic acid 4-fluorophenyl ester.

EXAMPLE 4

(a) A Grignard solution prepared from 3.59 g of magnesium and 16.75 ml of 1-bromo-4-fluorobenzene in 70 ml of tetrahydrofuran was treated dropwise at 0° C. within 30 minutes with a solution of 33.1 g of 4-[trans-4-[2-(1,3-dioxolan-2-yl)ethyl]cyclohexyl]cyclohexanone (prepared according to Example 1) in 90 ml of tetrahydrofuran. The reaction mixture was stirred at room temperature for a further 4 hours and then heated to boiling for 1.5 hours. Subsequently, the reaction mixture was left to cool, diluted with 100 ml of diethyl ether and washed with 80 ml of semi-saturated ammonium chloride solution. The aqueous phase was back-extracted with 100 ml of diethyl ether. The combined organic phases were washed three times with 60 ml of saturated sodium chloride solution each time, dried over sodium sulfate, filtered and evaporated. There were thus obtained 41.0 g of crude 1-[4-[trans-4-(2-(1,3-dioxolan-2-yl)ethyl]cyclohexyl]-1-hydroxycyclohexyl]-4-fluorobenzene.

(b) A solution of 41.0 g of crude 1-[4-[trans-4-(2-(1,3-dioxolan-2-yl)ethyl]cyclohexyl]-1-hydroxycyclohexyl]-4-fluorobenzene in 225 ml of m-xylene was treated with 15 g of potassium hydrogen sulfate and the mixture was heated to boiling for 11 hours while stirring. After cooling the salt was removed by filtration. The filtrate was diluted with 250 ml of diethyl ether, washed with 200 ml of saturated sodium hydrogen carbonate solution and twice with 150 ml of water each time, dried over sodium sulfate and concentrated. There were thus obtained 30.3 g of crude 1-[4-[trans-4-(2-(1,3-doxolan-2-yl)ethyl)cyclohexyl]-1-cyclohexenyl]-4-fluorobenzene.

(c) A solution of 31.5 g of crude 1-[4-[trans-4-(2-(1,3-dioxolan-2-yl)ethyl)cyclohexyl]-1-cyclohexenyl]-4-fluorobenzene and 0.5 ml of triethylamine in 1 l of toluene was hydrogenated at room temperature and normal pressure with 4.5 g of 5 percent palladium-charcoal until the hydrogen uptake came to a standstill. The catalyst was removed by filtration and the filtrate was evaporated. For the isomerization, the resulting 1-[4-[trans-4-(2-(1,3-dioxolan-2-yl)ethyl)-cyclohexyl]cyclohexyl]-4-fluorobenzene (31.1 g; cis/trans ratio about 1:1) was treated with a solution of 10.0 g of potassium tert.butylate in 310 ml of N,N-dimethylformamide and heated to 105° C. for 23 hours. Subsequently, the reaction mixture was poured on to 400 g of ice and 100 ml of saturated sodium hydrogen carbonate solution. The mixture was extracted once with 500 ml of diethyl ether and twice with 250 ml of diethyl ether each time. The organic phases were washed three times with 200 ml of water each time, dried over sodium sulfate, filtered and evaporated. There were thus obtained 30.5 g of predominantly solid 1-[trans-4-[trans-4-(2-(1,3-dioxolan-2-yl)ethyl)cyclohexyl]cyclohexyl]-4-fluorobenzene which was further processed without additional purification.

The following compounds can be prepared in an analogous manner:

1-[trans-4-[trans-4-(2-(1,3-Dioxolan-2-yl)ethyl)cyclohexyl]cyclohexyl]-3,4-difluorobenzene;
1-[trans-4-[trans-4-(2-(1,3-dioxolan-2-yl)ethyl)cyclohexyl]cyclohexyl]-3-chloro-4-fluorobenzene;
1-[trans-4-[trans-4-(2-(1,3-dioxolan-2-yl)ethyl)cyclohexyl]cyclohexyl]-3-fluoro-4-chlorobenzene;
1-[trans-4-[trans-4-(2-(1,3-dioxolan-2-yl)ethyl)cyclohexyl]cyclohexyl]-4-chlorobenzene;
1-[trans-4-[2-[trans-4-(2-(1,3-dioxolan-2-yl)ethyl)cyclohexyl]ethyl]cyclohexyl]-4-fluorobenzene;
1-[trans-4-[2-[trans-4-(2-(1,3-dioxolan-2-yl)ethyl)cyclohexyl]ethyl]cyclohexyl]-3,4-difluorobenzene;
1-[trans-4-[2-[trans-4-(2-(1,3-dioxolan-2-yl)ethyl)cyclohexyl]ethyl]cyclohexyl]-3-chloro-4-fluorobenzene;
1-[trans-4-[2-[trans-4-(2-(1,3-dioxolan-2-yl)ethyl)cyclohexyl]ethyl]cyclohexyl]-4-chlorobenzene;
1-[trans-4-[2-[trans-4-(2-(1,3-dioxolan-2-yl)ethyl)cyclohexyl]ethyl]cyclohexyl]-3-fluoro-4-chlorobenzene.

EXAMPLE 5

(a) A solution of 3.1 g of trans-4-[trans-4-[2-(1,3-dioxolan-2-yl)ethyl]cyclohexyl]cyclohexanecarboxylic acid (prepared according to Example 2) in 50 ml of dry diethyl ether is treated at 0° C. with 380 mg of lithium aluminium hydride and then heated to reflux for 4 hours. Thereafter, the reaction mixture is cooled, treated with ice-water and ammonium chloride solution and extracted with diethyl ether. The organic phase is washed with water, dried over magnesium sulfate, filtered and evaporated. The resulting crude product of [trans-4-[trans-4-(2-(1,3-dioxolan-2-yl)ethyl)cyclohexyl]cyclohexyl]methanol is used without additional purification.

(b) A solution of 2.96 g of crude [trans-4-[trans-4-(2-(1,3-dioxolan-2-yl)ethyl)cyclohexyl]cyclohexyl]methanol in 20 ml of dry pyridine is treated at 0° C. with 2.1 g of p-toluenesulfonyl chloride. The mixture is stirred at room temperature for 15 hours, then diluted with 200 ml of methylene chloride and washed several times with water. The organic phase is dried over magnesium sulfate, filtered and evaporated. Chromatographic purification of the resulting crude product on silica gel with ethyl acetate/petroleum ether (vol. 1:9) gives [trans-4-[trans-4-(2-(1,3-dioxolan-2-yl)ethyl)cyclohexyl]cyclohexyl]methyl p-toluenesulfonate.

(c) A solution of 0.33 g of potassium hydroxide in 7 ml of 95 percent ethanol is treated with 1.12 g of p-fluorophenol. Thereafter, the mixture is treated with a solution of 2.26 g of [trans-4-[trans-4-(2-(1,3-dioxolan-2-yl)ethyl)cyclohexyl]cyclohexyl]methyl p-toluenesulfonate in 23 ml of ethanol and stirred at 80° C. (bath temperature) for 24 hours. Subsequently, the reaction mixture is partitioned in 1N hydrochloric acid and methylene chloride. The organic phase is washed several times with water, dried over magnesium sulfate, filtered and evaporated. Chromatographic purification of the resulting crude product on silica gel with ethyl acetate/petroleum ether gives 1-[[trans-4-(trans-4-(2-(1,3-dioxolan-2-yl)ethyl)cyclohexyl]cyclohexyl]methoxy]-4-fluorobenzene.

The following compounds can be prepared in an analogous manner:

1[[trans-4-(trans-4-(2-(1,3-Dioxolan-2-yl)-ethyl)cyclohexyl)cyclohexyl]methoxy]-3,4-difluorobenzene;
1-[[trans-4-(trans-4-(2-(1,3-dioxolan-2-yl)-ethyl)cyclohexyl)cyclohexyl]methoxy]-3-chloro-4-fluorobenzene;
1-[[trans-4-(trans-4-(2-(1,3-dioxolan-2-yl)-ethyl)cyclohexyl)cyclohexyl]methoxy]-4-chlorobenzene;
1-[[trans-4-(trans-4-(2-(1,3-dioxolan-2-yl)-ethyl)cyclohexyl)cyclohexyl]methoxy]-3-fluoro-4-chlorobenzene.

EXAMPLE 6

(a) A solution of 3.1 g of pyridinium chlorochromate in 20 ml of methylene chloride is treated dropwise at room temperature with a solution of 3 g of [trans-4-[trans-4-(2-(1,3-dioxolan-2-yl)ethyl)cyclohexyl]cyclohexyl]methanol (preparable according to Example 5) in 10 ml of methylene chloride. The mixture is stirred for a further 1 hour, then diluted with 50 ml of diethyl ether and filtered. The filtrate is evaporated, the evaporation residue is taken up in 50 ml of diethyl ether and the solution obtained is again filtered. Chromatographic purification on silica gel with ethyl acetate/hexane (vol. 1:4) and crystallization from ethyl acetate/hexane finally gives trans-4-[trans-4-[2-(1,3-dioxolan-2-yl)ethyl]cyclohexyl]cyclohexanecarboxaldehyde.

(b) 3 g of p-fluorobenzyl-triphenylphosphonium bromide (preparable from p-fluorobenzyl bromide and triphenylphosphine) are suspended in 50 ml of tert.butyl methyl ether. The suspension is treated at room temperature with 0.75 g of potassium tert.butylate and stirred for 1.5 hours. Subsequently, the mixture is treated dropwise at 0° C. within 5 minutes with a solution of 1.40 g of trans-4-[trans-4-[2-(1,3-dioxolan-2-yl)ethyl]cyclohexyl]cyclohexanecarboxaldehyde in 25 ml of tert.butyl methyl ether and stirred at room temperature for a further 24 hours. Thereafter, the reaction mixture is taken up diethyl ether, washed several times with water, dried over magnesium sulfate, filtered and concentrated. Chromatographic purification of the resulting crude product on silica gel with ethyl acetate/petroleum ether (vol. 3:97) gives β-[trans-4-[trans-4-(2-(1,3-dioxolan-2-yl)ethyl)cyclohexyl]cyclohexyl]-4-fluorostyrene.

(c) A solution of 1 g of β-[trans-4-[trans-4-(2-(1,3-dioxolan-2-yl)ethyl)cyclohexyl]cyclohexyl]-4-fluorostyrene in 10 ml of toluene and 5 ml of ethanol is hydrogenated with 500 mg of 5 percent palladium-charcoal at room temperature and under normal pressure until the hydrogen uptake comes to a standstill. The black suspension is subsequently filtered. Evaporation of the filtrate gives 1-[2-[trans-4-[trans-4-(2-(1,3-dioxolan-2-yl)ethyl)cyclohexyl]cyclohexyl]ethyl]-4-fluorobenzene.

The following compounds can be prepared in an analogous manner:

1-[2-[trans-4-[trans-4-(2-(1,3-Dioxolan-2-yl)ethyl)cyclohexyl]cyclohexyl]ethyl]-3,4-difluorobenzene;
1-[2-[trans-4-[trans-4-(2-(1,3-dioxolan-2-yl)ethyl)cyclohexyl]cyclohexyl]ethyl]-3-chloro-4-fluorobenzene;
1-[2-[trans-4-[trans-4-(2-(1,3-dioxolan-2-yl)ethyl)cyclohexyl]cyclohexyl]ethyl]-4-chlorobenzene;
1-[2-[trans-4-[trans-4-(2-(1,3-dioxolan-2-yl)ethyl)cyclohexyl]cyclohexyl]ethyl]-3-fluoro-4-chlorobenzene.

EXAMPLE 7

A solution of 1.7 g of 4-fluorobenzoyl chloride in 5 ml of pyridine is treated with 2.8 g of trans-4-[trans-4-[2-(1,3-dioxolan-2-yl)ethyl]cyclohexyl]cyclohexanol (prepared according to Example 1) and stirred at room temperature for 12 hours. Thereafter, the reaction mixture is poured on to ice-water and extracted three times with diethyl ether. The organic phases are washed in succession with saturated sodium hydrogen carbonate solution, with 10 percent hydrochloric acid, with saturated sodium hydrogen carbonate solution and with water, then dried over magnesium sulfate, filtered and concentrated. Chromatographic purification of the resulting crude product on silica gel with ethyl acetate/petroleum ether (vol. 3:97) gives 4-fluorobenzoic acid trans-4-[trans-4-[2-(1,3-dioxolan-2-yl)ethyl]cyclohexyl]cyclohexyl ester.

The following compounds can be prepared in an analogous manner:

3,4-Difluorobenzoic acid trans-4-[trans-4-[2-(1,3-dioxolan-2-yl)ethyl]cyclohexyl]cyclohexyl ester;
3-chloro-4-fluorobenzoic acid trans-4-[trans-4-[2-(1,3-dioxolan-2-yl)ethyl]cyclohexyl]cyclohexyl ester;
4-chlorobenzoic acid trans-4-[trans-4-[2-(1,3-dioxolan-2-yl)ethyl]cyclohexyl]cyclohexyl ester;
3-fluoro-4-chlorobenzoic acid trans-4-[trans-4-[2-(1,3-dioxolan-2-yl)ethyl]cyclohexyl]cyclohexyl ester.

EXAMPLE 8

2.04 g of sodium hydride as an about 50% oily suspension are placed under nitrogen gasification and washed twice with pentane. There are then added to the sodium hydride 40 ml of dry tetrahydrofuran and a solution of 6.0 g of trans-4-[trans-4-[2-(1,3-dioxolan-2-yl)ethyl]cyclohexyl]cyclohexanol (prepared according to Example 2) in 30 ml of tetrahydrofuran. The mixture is stirred at room temperature for 30 minutes, then treated with 6.03 g of 4-fluorobenzyl bromide and heated to reflux for 2 hours. Subsequently, the reaction mixture is cooled, taken up in 200 ml of diethyl ether and washed three times with 200 ml of water each time. The organic phase is dried over magnesium sulfate, filtered and evaporated, whereby there is obtained trans-4-[trans-4-[2-(1,3-dioxolan-2-yl)ethyl]cyclohexyl]cyclohexyl 4-fluorobenzyl ether.

The following compounds can be prepared in an analogous manner:
trans-4-[trans-4-[2-(1,3-Dioxolan-2-yl)ethyl]cyclohexyl]cyclohexyl 3,4-difluorobenzyl ether;
trans-4-[trans-4-[2-(1,3-dioxolan-2-yl)ethyl]cyclohexyl]cyclohexyl 3-chloro-4-fluorobenzyl ether;
trans-4-[trans-4-[2-(1,3-dioxolan-2-yl)ethyl]cyclohexyl]cyclohexyl 4-chlorobenzyl ether;
trans-4-[trans-4-[2-(1,3-dioxolan-2-yl)ethyl]cyclohexyl]cyclohexyl 3-fluoro-4-chlorobenzyl ether.

EXAMPLE 9

(a) A mixture of 29.1 g of crude 1-[trans-4-[trans-4-(2-(1,3-dioxolan-2-yl)ethyl)cyclohexyl]cyclohexyl]-4-fluorobenzene, 200 ml of dioxan, 200 ml of glacial acetic acid and 400 ml of water was heated to slight boiling (bath temperature 115° C.) for 5 hours while stirring and gassing with nitrogen. The reaction mixture was then poured on to 500 g of ice. The aqueous phase was separated and extracted three times with 400 ml of diethyl ether each time. The combined organic phases were washed with 500 ml of saturated sodium hydrogen carbonate solution and with 500 ml of water, dried over sodium sulfate, filtered and concentrated. There were thus obtained 25.2 g of crude, solid 3-[trans-4-[trans-4-(4-fluorophenyl)cyclohexyl]cyclohexyl]propionaldehyde.

(b) A suspension of 9.1 g of methoxymethyl-triphenylphosphonium chloride in 50 ml of diethyl ether was treated with 2.85 g of potassium tert.butylate while gassing with nitrogen. The red suspension was stirred at room temperature for a further 30 minutes and then treated dropwise at 0° C. with a solution of 5.43 g of crude 3-[trans-4-[trans-4-(4-fluorophenyl)cyclohexyl]cyclohexyl]propionaldehyde in 30 ml of dry diethyl ether. The reaction mixture was stirred at room temperature for a further 90 minutes, then poured into 300 ml of hexane and filtered. Chromatographic purification of the concentrated filtrate on silica gel with hexane gave 4.9 g of solid 1-[trans-4-[trans-4-(4-methoxy-3-butenyl)cyclohexyl]cyclohexyl]-4-fluorobenzene.

(c) A mixture of 2.48 g of 1-[trans-4-[trans-4-(4-methoxy-3-butenyl)cyclohexyl]cyclohexyl]-4-fluorobenzene, 30 ml of dioxan, 20 ml of glacial acetic acid and 40 ml of water was heated to slight boiling (bath temperature 115° C.) while stirring and gassing with nitrogen. After cooling the suspension was diluted with 70 ml of water. The aqueous phase was separated and extracted three times with 80 ml of diethyl ether each time. The combined organic phases were washed twice with 1000 ml of water each time, dried over sodium sulfate, filtered and concentrated. There were thus obtained 2.3 g of solid 4-[trans-4-[trans-4-(4-fluorophenyl)cyclohexyl]cyclohexyl]butyraldehyde.

(d) A suspension of 5.19 g of methyl-triphenylphosphonium bromide in 80 ml of diethyl ether was treated with 1.55 g of potassium tert.butylate while gassing with nitrogen. The yellow suspension was stirred at room temperature for a further 45 minutes and then treated dropwise at 0° C. with a solution of 2.3 g of 4-[trans-4-[trans-4-(4-fluorophenyl)cyclohexyl]cyclohexyl]butyraldehyde. The reaction mixture was stirred at 0° C. for a further 2 hours and then diluted with 60 ml of water. The aqueous phase was separated and extracted twice with 60 ml of hexane each time. The combined organic phases were washed neutral with water, dried over sodium sulfate, filtered and concentrated. Chromatographic purification of the residue on silica gel with hexane gave 1.89 g of crude product. After two-fold recrystallization from acetone at −20° C. there were obtained 1.22 g of 1-[trans-4-[trans-4-(4-pentenyl)cyclohexyl]cyclohexyl]-4-fluorobenzene with m.p. (C-N) 65.7° C. and cl.p. (N-I) 129.7° C.

The 4-alkenyl compounds named in Example 3 as well as the following compounds can be prepared in an analogous manner:
1-[trans-4-[trans-4-(4-Pentenyl)cyclohexyl]cyclohexyl]-3,4-difluorobenzene;

1-[trans-4-[trans-4-(4-pentenyl)cyclohexyl]cyclohexyl-3-chloro-4-fluorobenzene;
1-[trans-4-[trans-4-(4-pentenyl)cyclohexyl]cyclohexyl-4-chlorobenzene;
1-[trans-4-[trans-4-(4-pentenyl)cyclohexyl]cyclohexyl-3-fluoro-4-chlorobenzene;
1-[trans-4-[2-(trans-4-(4-pentenyl)cyclohexyl)ethyl]cyclohexyl]-4-fluorobenzene;
1-[trans-4-[2-(trans-4-(4-pentenyl)cyclohexyl)ethyl]cyclohexyl]-3,4-difluorobenzene;
1-[trans-4-[2-(trans-4-(4-pentenyl)cyclohexyl)ethyl]cyclohexyl]-3-chloro-4-fluorobenzene;
1-[trans-4-[2-(trans-4-(4-pentenyl)cyclohexyl)ethyl]cyclohexyl]-4-chlorobenzene;
1-[trans-4-[2-(trans-4-(4-pentenyl)cyclohexyl)ethyl]cyclohexyl]-3-fluoro-4-chlorobenzene;
1-[[trans-4-(trans-4-(4-pentenyl)cyclohexyl)cyclohexyl]methoxy]-4-fluorobenzene;
1-[[trans-4-(trans-4-(4-pentenyl)cyclohexyl)cyclohexyl]methoxy]-3,4-difluorobenzene;
1-[[trans-4-(trans-4-(4-pentenyl)cyclohexyl)cyclohexyl]methoxy]-3-chloro-4-fluorobenzene;
1-[[trans-4-(trans-4-(4-pentenyl)cyclohexyl)cyclohexyl]methoxy]-4-chlorobenzene;
1-[[trans-4-(trans-4-(4-pentenyl)cyclohexyl)cyclohexyl]methoxy]-3-fluoro-4-chlorobenzene;
1-[2-[trans-4-(trans-4-(4-pentenyl)cyclohexyl)cyclohexyl]ethyl]-4-fluorobenzene;
1-[2-[trans-4-(trans-4-(4-pentenyl)cyclohexyl)cyclohexyl]ethyl]-3,4-difluorobenzene;
1-[2-[trans-4-(trans-4-(4-pentenyl)cyclohexyl)cyclohexyl]ethyl]-3-chloro-4-fluorobenzene;
1-[2-[trans-4-(trans-4-(4-pentenyl)cyclohexyl)cyclohexyl]ethyl]-4-chlorobenzene;
1-[2-[trans-4-(trans-4-(4-pentenyl)cyclohexyl)cyclohexyl]ethyl]-3-fluoro-4-chlorobenzene;
4-fluorobenzoic acid trans-4-[trans-4-(4-pentenyl)cyclohexyl]cyclohexyl ester;
3,4-difluorobenzoic acid trans-4-[trans-4-(4-pentenyl)cyclohexyl]cyclohexyl ester;
3-chloro-4-fluorobenzoic acid trans-4-[trans-4-(4-pentenyl)cyclohexyl]cyclohexyl ester;
4-chlorobenzoic acid trans-4-[trans-4-(4-pentenyl)cyclohexyl]cyclohexyl ester;
3-fluoro-4-chlorobenzoic acid trans-4-[trans-4-(4-pentenyl)cyclohexyl]cyclohexyl ester;
trans-4-[trans-4-(4-pentenyl)cyclohexyl]cyclohexyl 4-fluorobenzyl ether;
trans-4-[trans-4-(4-pentenyl)cyclohexyl]cyclohexyl 3,4-difluorobenzyl ether;
trans-4-[trans-4-(4-pentenyl)cyclohexyl]cyclohexyl 3-chloro-4-fluorobenzyl ether;
trans-4-[trans-4-(4-pentenyl)cyclohexyl]cyclohexyl 4-chlorobenzyl ether;
trans-4-[trans-4-(4-pentenyl)cyclohexyl]cyclohexyl 3-fluoro-4-chlorobenzyl ether;
1-[trans-4-[trans-4-(4Z-hexenyl)cyclohexyl]cyclohexyl]-4-fluorobenzene;
1-[trans-4-[trans-4-(4Z-hexenyl)cyclohexyl]cyclohexyl]-3,4-difluorobenzene;
1-[trans-4-[2-(trans-4-(4Z-hexenyl)cyclohexyl)ethyl]cyclohexyl]-4-fluorobenzene;
1-[trans-4-[2-(trans-4-(4Z-hexenyl)cyclohexyl)ethyl]cyclohexyl]-3,4-difluorobenzene;
1-[[trans-4-(trans-4-(4Z-hexenyl)cyclohexyl)cyclohexyl]methoxy]-4-fluorobenzene;
1-[[trans-4-(trans-4-(4Z-hexenyl)cyclohexyl)cyclohexyl]methoxy]-3,4-difluorobenzene;
1-[2-[trans-4-(trans-4-(4Z-hexenyl)cyclohexyl)cyclohexyl]ethyl]-4-fluorobenzene;
1-[2-[trans-4-(trans-4-(4Z-hexenyl)cyclohexyl)cyclohexyl]ethyl]-3,4-difluorobenzene;
4-fluorobenzoic acid trans-4-[trans-4-(4Z-hexenyl)cyclohexyl]cyclohexyl ester;
3,4-difluorobenzoic acid trans-4-[trans-4-(4Z-hexenyl)cyclohexyl]cyclohexyl ester;
trans-4-[trans-4-(4Z-hexenyl)cyclohexyl]cyclohexyl 4-fluorobenzyl ether;
trans-4-[trans-4-(4Z-hexenyl)cyclohexyl]cyclohexyl 3,4-difluorobenzyl ether.

The 3-alkenyl compounds set forth in Example 3 and further 3-alkenyl derivatives can also be prepared in an analogous manner by omitting steps (b) and (c).

EXAMPLE 10

The binary mixtures set forth hereinafter were prepared and investigated at 22° C. in a TN cell having a plate separation of 8 μm. The corresponding data for 4-(trans-4-pentylcyclohexyl)benzonitrile amounted to:
cl.p. 54.6° C., $V_{10}=1.62$ V, $t_{on}=30$ ms, $t_{off}=42$ ms, $\Delta n=0.120$.

MIXTURE 1

50 wt. % of trans-4-(3-butenyl)-1-(trans-4-ethoxycyclohexyl)cyclohexane,
50 wt. % of 4-(trans-4-pentylcyclohexyl)benzonitrile;
cl.p. 44.4° C., $V_{10}=1.66$ V, $t_{on}=21$ ms, $t_{off}=31$ ms, $\Delta n=0.082$.

MIXTURE 2

50 wt. % of trans-4-(3E-pentenyl)-1-(trans-4-methoxycyclohexyl)cyclohexane,
50 wt. % of 4-(trans-4-pentylcyclohexyl)benzonitrile;
m.p. 44.6° C., $V_{10}=1.55$ V, $t_{on}=22$ ms, $t_{off}=37$ ms, $\Delta n=0.084$.

MIXTURE 3

50 wt. % of trans-4-(3E-pentenyl)-1-(trans-4-ethoxycyclohexyl)cyclohexane,
50 wt. % of 4-(trans-4-pentylcyclohexyl)benzonitrile;
m.p. 57.4° C., $V_{10}=2.11$ V, $t_{on}=19$ ms, $t_{off}=28$ ms, $\Delta n=0.094$.

COMPARATIVE MIXTURE 4

50 wt. % of trans-4-butylcyclohexanecarboxylic acid trans-4-butylcyclohexyl ester,
50 wt. % of 4-(trans-4-pentylcyclohexyl)benzonitrile;
m.p. 40.2° C., $V_{10}=1.39$ V, $t_{on}=38$ ms, $t_{off}=63$ ms, $\Delta n=0.08$.

COMPARATIVE MIXTURE 5

50 wt. % of trans-4-pentyl-1-(trans-4-methoxycyclohexyl)cyclohexane,
50 wt. % of 4-(trans-4-pentylcyclohexyl)benzonitrile;
m.p. 39.7° C., $V_{10}=1.47$ V, $t_{on}=35$ ms, $t_{off}=42$ ms, $\Delta n=0.071$.

EXAMPLE 11

The mixtures set forth hereinafter were prepared and their properties were measured. Unless indicated otherwise, the measurement of the electro-optical data was effected at 22° C. in a TN cell having a plate separation of 6 μm.

MIXTURE A 10 wt. % of 4-[trans-4-(1E-propenyl)cyclohexyl]benzonitrile,
15 wt. % of 4-ethoxy-1-[trans-4-(3E-pentenyl)cyclohexyl]benzene,
12 wt. % of trans-4-[trans-4-(3-butenyl)cyclohexyl]cyclohexanecarbonitrile,
10 wt. % of trans-4-[trans-4-(3E-pentenyl)cyclohexyl]cyclohexanecarbonitrile,
8 wt. % of trans-4-[trans-4-(4-pentenyl)cyclohexyl]cyclohexanecarbonitrile,
8 wt. % of 1-[2-(trans-4-butylcyclohexyl)ethyl]-4-(trans-4-pentylcyclohexyl)benzene,
8 wt. % of trans-4-[trans-4-(3-butenyl)cyclohexyl]cyclohexanecarboxylic acid 4-fluorophenyl ester,
8 wt. % of trans-4-[trans-4-(3E-pentenyl)cyclohexyl]cyclohexanecarboxylic acid 4-fluorophenyl ester,
6 wt. % of trans-4-[trans-4-(4-pentenyl)cyclohexyl]cyclohexanecarboxylic acid 4-fluorophenyl ester,
15 wt. % of trans-4-(3-butenyl)-1-(trans-4-ethoxycyclohexyl)cyclohexane;
m.p.< −30° C. cl.p. 84° C., nematic; $V_{10}=2.35$ V, $t_{on}$ (22° C.)=15 ms, $t_{on}$(−20° C.)=309 ms, $t_{off}$(22° C.)=27 ms, $t_{off}$(−20° C.)=420 ms, $\Delta n=0.088$.

MIXTURE B 10 wt. % of 4-[trans-4-(1E-propenyl)cyclohexyl]benzonitrile,
8 wt. % of 4-(2E-butenyloxy)-1-(trans-4-propylcyclohexyl)benzene,
9 wt. % of trans-4-[trans-4-(3-butenyl)cyclohexyl]cyclohexanecarbonitrile,
6 wt. % of trans-4[trans-4-(4-pentenyl)cyclohexyl]cyclohexanecarbonitrile,
12 wt. % of trans-4-allyloxy-1-(trans-4-propylcyclohexyl)cyclohexane,
6 wt. % of r-1-cyano-1-(3-butenyl)-cis-4-(trans-4-pentylcyclohexyl)cyclohexane,
3 wt. % of 2-cyano-5-(trans-4-pentylcyclohexyl)pyrimidine,
3 wt. % of 4-(5-butyl-2-pyrimidinyl)benzonitrile,
6 wt. % of 4-[trans-5-(4-pentenyl)-m-dioxan-2-yl]benzonitrile,
7 wt. % of trans-4-propylcyclohexanecarboxylic acid 4-[trans-4-(3E-pentenyl)cyclohexyl]phenyl ester,
10 wt. % of 1-[2-(trans-4-butylcyclohexyl)ethyl]-4-(trans-4-pentylcyclohexyl)benzene,
4 wt. % of 4-[2-(trans-4-butylcyclohexyl)ethyl]-4'-(trans-4-pentylcyclohexyl)biphenyl,
4 wt. % of 4-[2-(trans-4-butylcyclohexyl)ethyl]-4'-[trans-4-(3E-pentenyl)cyclohexyl]biphenyl,
12 wt. % of trans-4-(3-butenyl)-1-(trans-4-methoxycyclohexyl)cyclohexane;
m.p.< −30° C., cl.p. 71° C., nematic; $V_{10}=1.80$ V; $t_{on}=(22°$ C.)=20 ms, $t_{on}$ (−20° C.)=330 ms, $t_{off}$ (22° C.)=37 ms, $t_{off}$(−20° C.)=440 ms, $\Delta n=0.090$.

MIXTURE C 8 wt. % of 4-(2E-butenyloxy)-1-(trans-4-propylcyclohexyl)benzene,
9 wt. % of trans-4-[trans-4-(3-butenyl)cyclohexyl]cyclohexanecarbonitrile,
10 wt. % of trans-4-[trans-4-(3E-pentenyl)cyclohexyl]cyclohexanecarbonitrile,
6 wt. % of trans-4-[trans-4-(4-pentenyl)cyclohexyl]cyclohexanecarbonitrile,
12 wt. % of trans-4-allyloxy-1-(trans-4-propylcyclohexyl)cyclohexane,
6 wt. % of r-1-cyano-1-(3-butenyl)-cis-4-(trans-4-pentylcyclohexyl)cyclohexane,
3 wt. % of 2-cyano-5-(trans-4-pentylcyclohexyl)pyrimidine,
3 wt. % of 4-(5-butyl-2-pyrimidinyl)benzonitrile,
6 wt. % of 4-[trans-5-(4-pentenyl)-m-dioxan-2-yl]benzonitrile,
7 wt. % of trans-4-propylcyclohexanecarboxylic acid 4-[trans-4-(3E-pentenyl)cyclohexyl]phenyl ester,
10 wt. % of 1-[2-(trans-4-butylcyclohexyl)ethyl]-4-(trans-4-pentylcyclohexyl)benzene,
4 wt. % of 4-[2-(trans-4-butylcyclohexyl)ethyl]-4'-(trans-4-pentylcyclohexyl)biphenyl,
4 wt. % of 4-[2-(trans-4-butylcyclohexyl)ethyl]-4'-[trans-4-(3E-pentenyl)cyclohexyl]biphenyl,
12 wt. % of trans-4-(3-butenyl)-1-(trans-4-methoxycyclohexyl)cyclohexane;
m.p.< −30° C., cl.p. 74° C., nematic; $V_{10}=2.01$ V, $t_{on}$ (22° C.)=34 ms, $t_{on}=(-20°$ C.)=470 ms, $t_{off}$(22° C.)=37 ms, $t_{off}$(−20° C.)=475 ms; $\Delta n=0.083$.

MIXTURE D 10 wt. % of 4-[trans-4-(1E-propenyl)cyclohexyl]benzonitrile,
9 wt. % of trans-4-[trans-4-(3-butenyl)cyclohexyl]cyclohexanecarbonitrile,
6 wt. % of trans-4-[trans-4-(4-pentenyl)cyclohexyl]cyclohexanecabonitrile,
12 wt. % of trans-4-allyloxy-1-(trans-4-propylcyclohexyl)cyclohexane,
6 wt. % of r-1-cyano-1-(3-butenyl)-cis-4-(trans-4-pentylcyclohexyl)cyclohexane,
3 wt. % of 2-cyano-5-(trans-4-pentylcyclohexyl)pyrimidine,
3 wt. % of 4-(5-butyl-2-pyrimidinyl)benzonitrile,
6 wt. % of 4-[trans-5-(4-pentenyl)-m-dioxan-2-yl]benzonitrile,
8 wt. % of 4-ethoxy-1-[2-(trans-4-pentylcyclohexyl)ethyl]benzene,
7 wt. % of trans-4-propylcyclohexanecarboxylic acid 4-[trans-4-(3E-pentenyl)cyclohexyl]phenyl ester,
10 wt. % of 1-[2-(trans-4-butylcyclohexyl)ethyl]-4-(trans-4-pentylcyclohexyl)benzene,
8 wt. % of 1-[trans-4-4-propylcyclohexyl)cyclohexyl]-4-fluorobenzene,
12 wt. % of trans-4-(3-butenyl)-1-(trans-4-methoxycyclohexyl)cyclohexane;
m.p.< −30° C., cl.p. 62° C., nematic; $V_{10}=1.79$ V, $t_{on}$ (22° C.)=27 ms, $t_{on}=(-20°$ C.)=480 ms, $t_{off}$ (22° C.)=50 ms, $t_{off}$(−20° C.)=480 ms, $\Delta n=0.081$.

MIXTURE E 10 wt. % of 4-[trans-4-(1E-propenyl)cyclohexyl]benzonitrile,
6 wt. % of 4-[trans-4-(3E-propenyl)cyclohexyl]benzonitrile,
12 wt. % of 4-ethoxy-1-[trans-4-(3E-pentenyl)cyclohexyl]benzene,
5 wt. % of trans-4-[trans-4-(3-butenyl)cyclohexyl]cyclohexanecarbonitrile,
7 wt. % of trans-4-[trans-4-(3E-pentenyl)cyclohexyl]cyclohexanecarbonitrile,
12 wt. % of trans-4-allyloxy-1-(trans-4-propylcyclohexyl)cyclohexane,
6 wt. % of 4-[trans-4-(3E-pentenyl)cyclohexyl]-4'-propylbiphenyl, 6 wt. % of trans-4-propylcyclohexanecarboxylic acid 4-[trans-4-(3E-pentenyl)cyclohexyl]phenyl ester,
10 wt. % of 1-[2-(trans-4-butylcyclohexyl)ethyl]-4-(trans-4-pentylcyclohexyl)benzene,
4 wt. % of 4-[2-(trans-4-butylcyclohexyl)ethyl]-4'-[trans-4-(3E-pentenyl)cyclohexyl]biphenyl,
8 wt. % of trans-4-[trans-4-(3-butenyl)cyclohexyl]cyclohexanecarboxylic acid 4-fluorophenyl ester,
4 wt. % of trans-4-[trans-4-(3E-pentenyl)cyclohexyl]cyclohexanecarboxylic acid 4-fluorophenyl ester,
10 wt. % of trans-4-(3E-pentenyl)-1-(trans-4-ethoxycyclohexyl)cyclohexane;

m.p. $< -30°$ C., cl.p. 100° C., nematic; $V_{10}=2.82$ V, $t_{on}$ (22° C.)=12 ms, $t_{on}=(-20°$ C.)=220 ms, $t_{off}$ (22° C.)=21 ms, $t_{off}(-20°$ C.)=330 ms; $\Delta n=0.105$.

MIXTURE F 9.40 wt. % of 4-[trans-4-(1E-propenyl)cyclohexyl]benzonitrile,
5.64 wt. % of 4-[trans-4-(3E-pentenyl)cyclohexyl]benzonitrile,
11.28 wt. % of 4-ethoxy-1-[trans-4-(3E-pentenyl)cyclohexyl]benzene,
4.70 wt. % of trans-4-[trans-4-(3-butenyl)cyclohexyl]cyclohexanecarbonitrile,
6.58 wt. % of trans-4-[trans-4-(3E-pentenyl)cyclohexyl]cyclohexanecarbonitrile,
11.28 wt. % of trans-4-allyloxy-1-(trans-4-propylcyclohexyl)cyclohexane,
6.00 wt. % of 2-cyano-5-(trans-4-butylcyclohexyl)pyrimidine,
5.64 wt. % of trans-4-propylcyclohexanecarboxylic acid 4-[trans-4-(3E-pentenyl)cyclohexyl]phenyl ester,
5.64 wt. % of 4-[trans-4-(3E-pentenyl)cyclohexyl]-4'-propylbiphenyl,
9.40 wt. % of 1-[2-(trans-4-butylcyclohexyl)ethyl]-4-(trans-4-pentenylcyclohexyl)benzene,
3.76 wt. % of 4-[2-(trans-4-butylcyclohexyl)ethyl]-4'-[trans-4-(3E-pentenyl)cyclohexyl]biphenyl,
7.52 wt. % of trans-4-[trans-4-(3-butenyl)cyclohexyl]cyclohexanecarboxylic acid 4-fluorophenyl ester,
3.76 wt. % of trans-4-[trans-4-(3E-pentenyl)cyclohexyl]cyclohexanecarboxylic acid 4-fluorophenyl ester,
9.40 wt. % of trans-4-(3E-pentenyl)-1-(trans-4-ethoxycyclohexyl)cyclohexane;

m.p. $< -30°$ C., cl.p. 95° C., nematic; $V_{10}=2.35$ V, $t_{on}$ (22° C.)=16 ms, $t_{on}=(-20°$ C.)=300 ms, $t_{off}$ (22° C.)=24 ms, $t_{off}(-20°$ C.)=350 ms, $\Delta n=0.104$.

MIXTURE G 10 wt. % of 4-[trans-4-(1E-propenyl)cyclohexyl]benzonitrile,
12 wt. % of 4-(2E-butenyloxy)-1-(trans-4-propylcyclohexyl)benzene,
5 wt. % of trans-4-[trans-4-(3-butenyl)cyclohexyl]cyclohexanecarbonitrile,
7 wt. % of trans-4-[trans-4-(3E-pentenyl)cyclohexyl]cyclohexanecarbonitrile,
6 wt. % of trans-4-[trans-4-(4-pentenyl)cyclohexyl]cyclohexanecarbonitrile,
12 wt. % of trans-4-allyloxy-1-(trans-4-propylcyclohexyl)cyclohexane,
8 wt. % of trans-4-propylcyclohexanecarboxylic acid 4-[trans-4-(3E-pentenyl)cyclohexyl]phenyl ester,
10 wt. % of 1-[2-(trans-4-butylcyclohexyl)ethyl]-4-(trans-4-pentylcyclohexyl)benzene,
5 wt. % of 4-[2-(trans-4-butylcyclohexyl)ethyl]-4-(trans-4-pentylcyclohexyl)biphenyl,
3 wt. % of 5-(trans-4-pentylcyclohexyl)-2-[4-(trans-4-propylcyclohexyl)phenyl]pyrimidine,
4 wt. % of trans-4-[trans-4-(3-butenyl)cyclohexyl]cyclohexanecarboxylic acid 4-fluorophenyl ester,
8 wt. % of trans-4-[trans-4-(3E-pentenyl)cyclohexyl]cyclohexanecarboxylic acid 4-fluorophenyl ester,
10 wt. % of trans-4-(3E-pentenyl)-1-(trans-4-ethoxycyclohexyl)cyclohexane;

m.p. $< -30°$ C., cl.p. 109° C., nematic; $V_{10}=2.84$ V, $t_{on}$ (22° C.)=16 ms, $t_{on}=(-20°$ C.)=336 ms, $t_{off}$ (22° C.)=26 ms, $t_{off}(-20°$ C.)=370 ms, $\Delta n=0.096$.

MIXTURE H 15 wt. % of trans-4-[trans-4-(3-butenyl)cyclohexyl]cyclohexanecarbonitrile,
12 wt. % of trans-4-[trans-4-(3E-pentenyl)cyclohexyl]cyclohexanecarbonitrile,
10 wt. % of trans-4-[trans-4-(4-pentenyl)cyclohexyl]cyclohexanecarbonitrile,
10 wt. % of 4-[trans-4-(1E-propenyl)cyclohexyl]benzonitrile,
20 wt. % of trans-4-allyloxy-1-(trans-4-propylcyclohexyl)cyclohexane,
10 wt. % of trans-4-[trans-4-(3-butenyl)cyclohexyl]cyclohexanecarboxylic acid 4-fluorophenyl ester,
8 wt. % of trans-4-[trans-4-(4-pentenyl)cyclohexyl]cyclohexanecarboxylic acid 4-fluorophenyl ester,
15 wt. % of 4-ethoxy-1-[trans-4-(3E-pentenyl)cyclohexyl]benzene, m.p. $< -30°$ C., cl.p. (N-I) 71° C.; $V_{10}=2.10$ V, $t_{on}$ (22° C.)=19 ms, $t_{on}(-20°$ C.)=477 ms, $t_{off}(22°$ C.)=31 ms, $t_{off}(-20°$ C.)=391 ms, $\Delta n=0.084$.

EXAMPLE 12

The diamagnetic anisotropy of the compounds in accordance with the invention is approximately zero and the absolute value of the dielectric anisotropy is small. In order to investigate the properties there were therefore prepared binary mixtures (BM) with low-viscous, non-polar phenylcyclohexanes in order to increase the diamagnetic anisotropy. The measurement of the physical properties was effected at a temperature 10° C. below the respective clearing point unless indicated otherwise. Values having an asterisk * are extrapolated values. The corresponding data for the phenylcyclohexanes used are:

for 4-(2E-butenyl)oxy-1-(trans-4-propylcyclohexyl)benzene: m.p. (C-N) 42.4° C., cl.p. (N-I) 57.5° C., $k_{11}=10.9$ pN, $k_{22}=5.60$ pN, $k_{33}=12.4$ pN, $\Delta o=-0.33$, $\Delta n=0.090$, $\eta=5.3$ cp, $\eta(22°$ C.)=13.5 cp*, $\gamma_1=22$ cp, $\gamma_1$ (22° C.)=86 cp*;

for 4-ethoxy-1-[trans-4-(3E-pentenyl)cyclohexyl]benzene: m.p. (C-N) 49.4° C., cl.p. (N-I) 61.8° C., $k_{11}=10.1$ pN, $k_{22}=4.82$ pN, $k_{33}=15.7$ pN, $\Delta\epsilon=-0.27$, $\Delta n=0.095$, $\eta=4.7$ cp, $\gamma_1=25$ cp.

BM-1

50 mol % of trans-4-(3-butenyl)-1-(trans-4-ethoxycyclohexyl)cyclohexane,
50 mol % of 4-(2E-butenyl)oxy-1-(trans-4-propylcyclohexyl)benzene;

m.p. $<15°$ C., cl.p. (N-I) 44.5° C., $k_{11}=7.07$ pN, $k_{22}=3.78$ pN, $k_{33}=8.08$ pN, $\Delta\epsilon=-0.31$, $\Delta n=0.065$, $\eta=6.8$ cp, $\eta(22°$ C.)=10.3 cp, $\gamma_1=41$ cp, $\gamma_1$ (22° C.)=62 cp.

BM-2

50 mol % of trans-4-(3E-pentenyl)-1-(trans-4-ethoxycyclohexyl)-cyclohexane, 50 mol % of 4-(2E-butenyl)oxy-1-(trans-4-propylcyclohexyl)benzene;

m.p. <15° C., cl.p. (N-I) 58.6° C., $k_{11}=8.71$ pN, $k_{22}=4.13$ pN, $k_{33}=11.2$ pN, $\Delta\epsilon=-0.21$, $\Delta n=0.070$, $\eta=5.2$ cp, $\eta(22°$ C.$)=11.4$ cp, $\gamma_1=20$ cp, $\gamma_1$ (22° C.)=66 cp.

BM-3

50 mol % of trans-4-(3E-pentenyl)-1-(trans-4-methoxycyclohexyl)cyclohexane, 50 mol % of 4-(2E-butenyl)oxy-1-(trans-4-propylcyclohexyl)benzene;

m.p. <15° C., cl.p. (N-I) 45.0° C., $k_{11}=6.73$ pN, $k_{22}=3.69$ pN, $k_{33}=7.94$ pN, $\Delta\epsilon=-0.20$, $\Delta n=0.066$, $\eta=7.8$ cp, $\eta(22°$ C.$)=11.7$ cp, $\gamma_1=27$ cp, $\gamma_1$ (22° C.)=53 cp.

BM-4

50 mol % of trans-4-(3-butenyl)-1-(trans-4-ethoxycyclohexyl)cyclohexane, 50 mol % of 4-ethoxy-1-[trans-4-(3E-pentenyl)cyclohexyl]benzene;

m.p. <15° C., cl.p. (N-I) 48.2° C., $k_{11}=7.16$ pN, $k_{22}=4.05$ pN, $k_{33}=9.88$ pN, $\Delta\epsilon=-0.31$, $\Delta n=0.068$, $\eta=6.3$ cp, $\eta(22°$ C.$)=9.8$ cp, $\gamma_1=22$ cp, $\gamma_1$ (22° C.)=47 cp.

We claim:

1. A compound of the formula

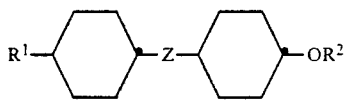

I wherein Z is a single covalent bond or —$CH_2CH_2$—, $R^1$ is 1E-alkenyl with 2–10 carbon atoms or 3E-alkenyl with 4–10 carbon atoms and $R^2$ is alkyl with 1–10 carbon atoms, 2E-alkenyl with 3–10 carbon atoms or 3-alkenyl with 4–10 carbon atoms.

2. The compound of claim 1, wherein $R^1$ is 1E-alkenyl with 2–7 carbon atoms or 3E-alkenyl with 4–7 carbon atoms.

3. The compound of claim 1, wherein $R^2$ is alkyl with 1–6 carbon atoms, 2E-alkenyl with 3–6 carbon atoms or 3-alkenyl with 4–6 carbon atoms.

4. The compound of claim 1, wherein $R^1$ and $R^2$ each are straight-chain residues as defined in claim 1.

5. A liquid crystalline mixture with at least 2 components, wherein at least one of such components is a compound of formula

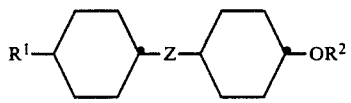

I wherein Z is a single covalent bond or —$CH_2CH_2$—, $R^1$ is 1E-alkenyl with 2–10 carbon atoms or 3E-alkenyl with 4–10 carbon atoms and $R^2$ is alkyl with 1–10 carbon atoms, 2E-alkenyl with 3–10 carbon atoms or 3-alkenyl with 4–10 carbon atoms.

6. The liquid crystalline mixture of claim 5, which contains at least one compound of formula I and one or more compounds having positive dielectric anisotropy.

7. The liquid crystalline mixture of claim 5, which contains at least one compound of formula I and at least one compound selected from the group of compounds of the formulas

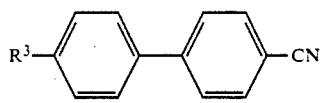

II

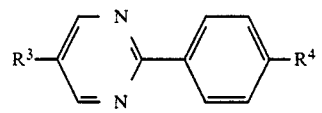

III

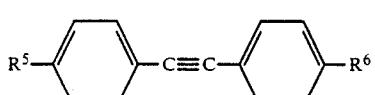

IV

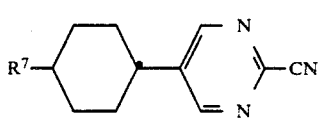

V

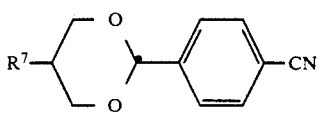

VI

-continued
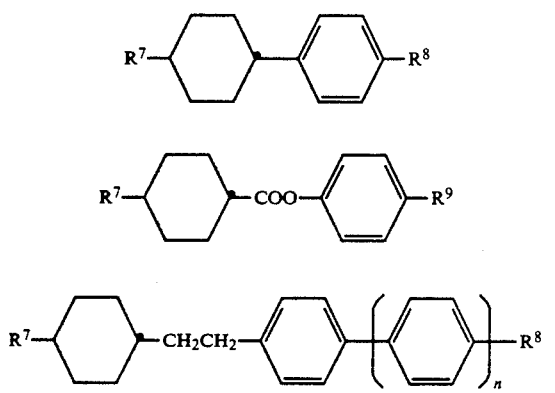

-continued

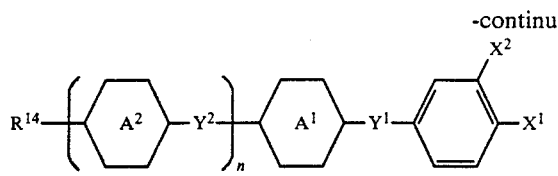

XIX wherein $R^3$ is alkyl, 3E-alkenyl or 4-alkenyl; $R^4$ is cyano or fluoro; $R^5$ and $R^6$ each independently are alkyl or alkoxy; $R^7$ and $R^{13}$ each independently are alkyl, 1E-alkenyl, 3E-alkenyl or 4-alkenyl; $R^8$ is cyano, alkyl, 1E-alkenyl, 3E-alkenyl, 4-alkenyl, alkoxy, 2E-alkenyloxy or 3-alkenyloxy; $R^9$ is alkoxy, 2E-alkenyloxy or 3-alkenyloxy; n is for the integer 0 or 1; Z is a single covalent bond or —CH$_2$CH$_2$—; $R^{10}$ is cyano, alkyl, 1E-alkenyl, 3E-alkenyl or 4-alkenyl; $R^{11}$ is alkyl or 4-alkenyl; $R^{12}$ is alkoxy, 2E-alkenyloxy or 3-alkenyloxy; $X^1$ is fluorine or chlorine and $X^2$ is hydrogen, fluorine or chlorine; $R^{14}$ is alkyl, 3E-alkenyl, 4-alkenyl, alkoxy, 2E-alkenyloxy or 3-alkenyloxy; one of the groups $Y^1$ and $Y^2$ is a single covalent bond, —COO—, —OOC—, —CH$_2$CH$_2$, —CH$_2$O— or —OCH$_2$— and the other of the groups $Y^1$ and $Y^2$ is a single covalent bond; and each of rings $A^1$ and $A^2$ individually is an unsubstituted or substituted substituent of trans-1,4-cyclohexylene, trans-1,4-cyclohexylene in which 2 non-adjacent CH$_2$ groups are replaced by oxygen, 1,4-phenylene, or 1,4-phenylene in which 1 CH group or 2 CH groups are replaced by nitrogen, the substituted substituent being substituted with at least one of cyano, lower alkyl or halo.

8. The liquid crystalline mixture of claims 5, wherein the amount of compound I in the total mixture amounts to about 1 to about 70 wt. %.

9. The liquid crystalline mixture of claims 8, wherein the amount of compound I in the total mixture amounts to about 3 to about 40 wt. %.

10. An electro-optical cell comprising:
(a) two plate means;
(b) liquid crystal means disposed between the two plate means and including a compound of the formula:

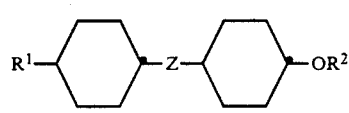

I wherein Z is a single covalent bond or —CH$_2$CH$_2$—, $R^1$ is 1E-alkenyl with 2–10 carbon atoms or 3E-alkenyl with 4–10 carbon atoms and $R^2$ is alkyl with 1–10 carbon atoms, 2E-alkenyl with 3–10 carbon atoms or 3-alkenyl with 4–10 carbon atoms; and (c) means for applying an electrical potential to said plate means.

11. The compound of claim 1, trans-4-(3-butenyl)-1-(trans-4-methoxycyclohexyl)cyclohexane.

12. The compound of claim 1, trans-4-(3-butenyl)-1-(trans-4-ethoxycyclohexyl)cyclohexane.

13. The compound of claim 1, trans-4-(3E-pentenyl)-1-(trans-4-methoxycyclohexyl)cyclohexane.

14. The compound of claim 1, trans-4-(3E-pentenyl)-1-(trans-4-ethoxycyclohexyl)cyclohexane.

15. The compound of claim 1, trans-4-(1E-propenyl)-1-(trans-4-methoxycyclohexyl)cyclohexane.

* * * * *